US011844831B2

(12) United States Patent
Young

(10) Patent No.: US 11,844,831 B2
(45) Date of Patent: Dec. 19, 2023

(54) AFRICAN SWINE FEVER (ASF) VIRUS VACCINES

(71) Applicant: VST LLC, Brookings, SD (US)

(72) Inventor: Alan Young, Brookings, SD (US)

(73) Assignee: VST LLC, Brookings, SD (US)

(*) Notice: Subject to any disclaimer, the term of this patent is extended or adjusted under 35 U.S.C. 154(b) by 147 days.

(21) Appl. No.: 17/557,848

(22) Filed: Dec. 21, 2021

(65) Prior Publication Data

US 2022/0193218 A1 Jun. 23, 2022

Related U.S. Application Data

(60) Provisional application No. 63/128,318, filed on Dec. 21, 2020.

(51) Int. Cl.

| | |
|---|---|
| ***A61K 39/12*** | (2006.01) |
| ***A61K 39/39*** | (2006.01) |
| ***A61P 31/20*** | (2006.01) |
| *A61K 39/00* | (2006.01) |

(52) U.S. Cl.

CPC .............. *A61K 39/12* (2013.01); *A61K 39/39* (2013.01); *A61P 31/20* (2018.01); *A61K 2039/545* (2013.01); *A61K 2039/552* (2013.01); *A61K 2039/555* (2013.01)

(58) Field of Classification Search

None

See application file for complete search history.

(56) References Cited

U.S. PATENT DOCUMENTS

| | | | | |
|---|---|---|---|---|
| 2021/0085776 | A1* | 3/2021 | Gladue | A61P 31/20 |
| 2022/0193218 | A1* | 6/2022 | Young | A61K 39/12 |

OTHER PUBLICATIONS

Lopera-Madrid et al. (Veterinary Immunology and Immunopathogy. 2017; 185: 20-33).*

Ravilov et al. (Frontiers in Veterinary Science. 2022 (9): 830244).*

Zhang et al. (Frontiers in Microbiology. 2023; 14: 1139494).*

Barderas et al. (Archives of Virology. 2001; 146: 1681-1691).*

* cited by examiner

*Primary Examiner* — Shanon A. Foley

(57) ABSTRACT

The present invention describes immunogenic compositions containing immunogenic polypeptides of African Swine Fever (ASF) virus, including immunogenic compositions containing antigens other than ASF viral antigens, including antigens that may be used in immunization against pathogens that cause diarrheal diseases. Methods of eliciting an immune response with the immunogenic compositions as disclosed and methods of treating an ASF infection are also described.

20 Claims, No Drawings

Specification includes a Sequence Listing.

SEQUENCE LISTING

```
<160> NUMBER OF SEQ ID NOS: 17

<210> SEQ ID NO 1
<211> LENGTH: 1213
<212> TYPE: DNA
<213> ORGANISM: African swine fever virus
<220> FEATURE:
<221> NAME/KEY: misc_feature
<222> LOCATION: (1)..(6)
<223> OTHER INFORMATION: EcoRI
<220> FEATURE:
<221> NAME/KEY: misc_feature
<222> LOCATION: (1)..(6)
<223> OTHER INFORMATION: EcoRI Restriction Site
<220> FEATURE:
<221> NAME/KEY: misc_feature
<222> LOCATION: (1159)..(1175)
<223> OTHER INFORMATION: TEV Protease Site
<220> FEATURE:
<221> NAME/KEY: misc_feature
<222> LOCATION: (1176)..(1205)
<223> OTHER INFORMATION: HIS Tag + Stop Codon
<220> FEATURE:
<221> NAME/KEY: misc_feature
<222> LOCATION: (1206)..(1213)
<223> OTHER INFORMATION: NotI Restriction Site

<400> SEQUENCE: 1

gaattcatgg attctgaatt ttttcaaccg gtttatccgc ggcattatgg tgagtgtttg      60

tcaccagtca ctacaccaag cttcttctcc acacatatgt atactattct cattgctatc     120

gtggtcttag tcatcattat catcgttcta atctacttat tctcttcaag aaagaaaaaa     180

gctgctgcta ttgaggagga agatatacag tttataaatc cttatcaaga tcagcagtgg     240

gtagaagtca ctccacaacc aggtacctct aaaccagctg gagcgactac agcaagtgta     300

ggcaagccag tcacgggcag accggcaaca aacagaccag caacaaacaa accagttacg     360

gacaacccag ttacggacag actagtcatg gcaactggcg ggccggcagc cgctatggat     420

tttattttaa atatatccat gaaaatggag gtcatcttca aaacggattt aagatcatct     480

tcacaagttg tgtttcatgc gggtagcctg tataattggt tttctgttga gattatcaat     540

agcggtagaa ttgttacgac cgctataaaa acattgctta gtactgttaa gtatgatatt     600

gtgaaatctg ctcgtatata tgcagggcaa gggtatactg aacatcaggc tcaagaagaa     660

tggaatatga ttctgcatgt gctgtttgaa gaggagacgg aatcctcagc atcttcggag     720
```

-continued aacattcatg aaaaaaatga taatgaaacc aatgaatgca catcctcctt tgaaacgttg 780
tttgagcaag agccctcatc ggaggtacct aaagactcca agctgtatat gcttgcacaa 840
aagactgtgc aacatattga acaatatgga aaggcacctg attttaacaa ggttattaga 900
gcacataatt ttattcaaac catttatgga acccctctaa aggaagaaga aaaagaggtg 960
gtaagactca tggttattaa acttttaaaa aaaataagct tttatctcac ctacattgca 1020
gccgctagtg ctcctgctca tccggctgag ccttacacga cagtcactac tcagaacact 1080
gcttcacaaa caatgtcggc tattgaaaat ttacgacaaa gaaacaccta tacgcataaa 1140
gacctagaaa actccttgaa aggcgagaac ctgtattttc aaggccacca tcatcaccat 1200
cactagcggc cgc 1213

<210> SEQ ID NO 2
<211> LENGTH: 18
<212> TYPE: DNA
<213> ORGANISM: Artificial Sequence
<220> FEATURE:
<223> OTHER INFORMATION: PCR Primer

<400> SEQUENCE: 2
gtctgcgagc agttgttt 18

<210> SEQ ID NO 3
<211> LENGTH: 22
<212> TYPE: DNA
<213> ORGANISM: Artificial Sequence
<220> FEATURE:
<223> OTHER INFORMATION: PCR Primer

<400> SEQUENCE: 3
cattcttctt gagcctgatg tt 22

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
catgcgggta gcctgtataa 20

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
cgctctaaca taccacccta aa 22

<210> SEQ ID NO 6
<211> LENGTH: 399
<212> TYPE: PRT
<213> ORGANISM: African swine fever virus

<400> SEQUENCE: 6

Met Asp Ser Glu Phe Phe Gln Pro Val Tyr Pro Arg His Tyr Gly Glu
1 5 10 15

Cys Leu Ser Pro Val Thr Thr Pro Ser Phe Phe Ser Thr His Met Tyr
20 25 30

```
Thr Ile Leu Ile Ala Ile Val Val Leu Val Ile Ile Ile Ile Val Leu
        35                  40                  45

Ile Tyr Leu Phe Ser Ser Arg Lys Lys Lys Ala Ala Ala Ile Glu Glu
    50                  55                  60

Glu Asp Ile Gln Phe Ile Asn Pro Tyr Gln Asp Gln Gln Trp Val Glu
65                  70                  75                  80

Val Thr Pro Gln Pro Gly Thr Ser Lys Pro Ala Gly Ala Thr Thr Ala
                85                  90                  95

Ser Val Gly Lys Pro Val Thr Gly Arg Pro Ala Thr Asn Arg Pro Ala
            100                 105                 110

Thr Asn Lys Pro Val Thr Asp Asn Pro Val Thr Asp Arg Leu Val Met
        115                 120                 125

Ala Thr Gly Gly Pro Ala Ala Ala Met Asp Phe Ile Leu Asn Ile Ser
    130                 135                 140

Met Lys Met Glu Val Ile Phe Lys Thr Asp Leu Arg Ser Ser Ser Gln
145                 150                 155                 160

Val Val Phe His Ala Gly Ser Leu Tyr Asn Trp Phe Ser Val Glu Ile
                165                 170                 175

Ile Asn Ser Gly Arg Ile Val Thr Thr Ala Ile Lys Thr Leu Leu Ser
            180                 185                 190

Thr Val Lys Tyr Asp Ile Val Lys Ser Ala Arg Ile Tyr Ala Gly Gln
        195                 200                 205

Gly Tyr Thr Glu His Gln Ala Gln Glu Glu Trp Asn Met Ile Leu His
    210                 215                 220

Val Leu Phe Glu Glu Glu Thr Glu Ser Ser Ala Ser Ser Glu Asn Ile
225                 230                 235                 240

His Glu Lys Asn Asp Asn Glu Thr Asn Glu Cys Thr Ser Ser Phe Glu
                245                 250                 255

Thr Leu Phe Glu Gln Glu Pro Ser Ser Glu Val Pro Lys Asp Ser Lys
            260                 265                 270

Leu Tyr Met Leu Ala Gln Lys Thr Val Gln His Ile Glu Gln Tyr Gly
        275                 280                 285

Lys Ala Pro Asp Phe Asn Lys Val Ile Arg Ala His Asn Phe Ile Gln
    290                 295                 300

Thr Ile Tyr Gly Thr Pro Leu Lys Glu Glu Glu Lys Glu Val Val Arg
305                 310                 315                 320

Leu Met Val Ile Lys Leu Leu Lys Lys Ile Ser Phe Tyr Leu Thr Tyr
                325                 330                 335

Ile Ala Ala Ala Ser Ala Pro Ala His Pro Ala Glu Pro Tyr Thr Thr
            340                 345                 350

Val Thr Thr Gln Asn Thr Ala Ser Gln Thr Met Ser Ala Ile Glu Asn
        355                 360                 365

Leu Arg Gln Arg Asn Thr Tyr Thr His Lys Asp Leu Glu Asn Ser Leu
    370                 375                 380

Lys Gly Glu Asn Leu Tyr Phe Gln Gly His His His His His His
385                 390                 395
```

<210> SEQ ID NO 7
<211> LENGTH: 1995
<212> TYPE: DNA
<213> ORGANISM: African swine fever virus

<400> SEQUENCE: 7

```
gaattcatgg catcaggagg agctttttgt cttattgcta acgatgggaa ggccgacaag     60
```

-continued

```
attatattgg cccaagactt gctgaatagc aggatctcta acattaaaaa tgtgaacaaa    120
agttatggga aacccgatcc cgaacccact ttgagtcaaa tcgaagaaac acatttggtg    180
cattttaatg cgcattttaa gccttatgtt ccagtagggt ttgaatacaa taaagtacgc    240
ccgcatacgg gtacccccac cttgggaaac aagcttacct ttggtattcc ccagtacgga    300
gactttttcc atgatatggt gggccatcat atattgggtg catgtcattc atcctggcag    360
gatgctccga ttcagggcac gtcccagatg ggggcccatg ggcagcttca aacgtttcct    420
cgcaacggat atgactggga caaccaaaca cccttagagg gcgccgttta cacgcttgta    480
gatccttttg gaagacccat tgtacccggc acaaagaatg cgtaccgaaa cttggtttac    540
tactgcgaat accccggaga acgactttat gaaaacgtaa gattcgatgt aaatggaaat    600
tccctagacg aatatagttc ggatgtcacc agcgttgtgc gcaaattttg catcccaggg    660
gataaaatga ctggatataa gcacttggtt ggccaggagg tatcggtgga gggaaccagt    720
ggccctctcc tatgcaacat tcatgatttg cacaagccgc accaaagcaa acctattctt    780
accgatgaaa atgatacgca gcgaacgtgt agccatacca acccgaaatt tctttcacag    840
cattttcccg agaactctca caatatccaa acagcaggta aacaagatat tactcctatc    900
acggacgcaa cgtatctgga cataagacgt aatgttcatt acagctgtaa tggacctcaa    960
acccctaaat actatcagcc ccctcttgcg ctctggatta agttgcgctt ttggtttaat   1020
gagaacgtga accttgctat tccctcagta tccattccct tcggcgagcg ctttatcacc   1080
ataaagcttg catcgcaaaa ggatttggtg aatgaatttc ctggactttt tgtacgccag   1140
tcacgtttta tagctggacg ccccagtaga cgcaatatac gctttaaacc atggtttatc   1200
ccaggagtca ttaatgaaat ctcgctcacg aataatgaac ttacatcaat aacctgtttg   1260
taacccctga aatacacaac ctttttgtaa aacgcgttcg cttttcgctg atacgtgtcc   1320
ataaaacgca ggtgacccac accaacaata accaccacga tgaaaaacta atgtctgctc   1380
ttaaatggcc cattgaatat atgtttatag gattaaaacc tacctggaac atctccgatc   1440
aaaatcctca tcaacaccga gattggcaca agttcggaca tgttgttaac gccattatgc   1500
agcccactca ccacgcagag ataagctttc aggatagaga tacagctctt ccagacgcat   1560
gttcatctat atctgatatt agccccgtta cgtatccgat cacattacct attaaaaaca   1620
tttccgtaac tgctcatggt atcaatctta tcgataaatt tccatcaaag ttctgcagct   1680
cttacatacc cttccactac ggaggcaatg cgattaaaac ccccgatgat ccgggtgcga   1740
tgatgattac ctttgctttg aagccacggg aggaatacca acccagtggt catattaacg   1800
tatccagagc aagagaattt tatattagtt gggacacgga ttacgtgggg tctatcacta   1860
cggctgatct tgtggtatcg gcatctgcta ttaactttct tcttcttcag aacggttcag   1920
ctgtgctgcg ttacagtacc aaaggcgaga acctgtattt tcaaggccac catcatcacc   1980
atcactagcg gccgc                                                    1995
```

<210> SEQ ID NO 8
<211> LENGTH: 661
<212> TYPE: PRT
<213> ORGANISM: African swine fever virus

<400> SEQUENCE: 8

```
Met Ala Ser Gly Gly Ala Phe Cys Leu Ile Ala Asn Asp Gly Lys Ala
1               5                   10                  15

Asp Lys Ile Ile Leu Ala Gln Asp Leu Leu Asn Ser Arg Ile Ser Asn
```

-continued

```
            20                  25                  30

Ile Lys Asn Val Asn Lys Ser Tyr Gly Lys Pro Asp Pro Glu Pro Thr
        35                  40                  45

Leu Ser Gln Ile Glu Glu Thr His Leu Val His Phe Asn Ala His Phe
    50                  55                  60

Lys Pro Tyr Val Pro Val Gly Phe Glu Tyr Asn Lys Val Arg Pro His
65                  70                  75                  80

Thr Gly Thr Pro Thr Leu Gly Asn Lys Leu Thr Phe Gly Ile Pro Gln
                85                  90                  95

Tyr Gly Asp Phe Phe His Asp Met Val Gly His His Ile Leu Gly Ala
            100                 105                 110

Cys His Ser Ser Trp Gln Asp Ala Pro Ile Gln Gly Thr Ser Gln Met
        115                 120                 125

Gly Ala His Gly Gln Leu Gln Thr Phe Pro Arg Asn Gly Tyr Asp Trp
    130                 135                 140

Asp Asn Gln Thr Pro Leu Glu Gly Ala Val Tyr Thr Leu Val Asp Pro
145                 150                 155                 160

Phe Gly Arg Pro Ile Val Pro Gly Thr Lys Asn Ala Tyr Arg Asn Leu
                165                 170                 175

Val Tyr Tyr Cys Glu Tyr Pro Gly Glu Arg Leu Tyr Glu Asn Val Arg
            180                 185                 190

Phe Asp Val Asn Gly Asn Ser Leu Asp Glu Tyr Ser Ser Asp Val Thr
        195                 200                 205

Thr Leu Val Arg Lys Phe Cys Ile Pro Gly Asp Lys Met Thr Gly Tyr
    210                 215                 220

Lys His Leu Val Gly Gln Glu Val Ser Val Glu Gly Thr Ser Gly Pro
225                 230                 235                 240

Leu Leu Cys Asn Ile His Asp Leu His Lys Pro His Gln Ser Lys Pro
                245                 250                 255

Ile Leu Thr Asp Glu Asn Asp Thr Gln Arg Thr Cys Ser His Thr Asn
            260                 265                 270

Pro Lys Phe Leu Ser Gln His Phe Pro Glu Asn Ser His Asn Ile Gln
        275                 280                 285

Thr Ala Gly Lys Gln Asp Ile Thr Pro Ile Thr Asp Ala Tyr Thr Leu
    290                 295                 300

Asp Ile Arg Arg Asn Val His Tyr Ser Cys Asn Gly Pro Gln Thr Pro
305                 310                 315                 320

Lys Tyr Tyr Gln Pro Pro Leu Ala Leu Trp Ile Lys Leu Arg Phe Trp
                325                 330                 335

Phe Asn Glu Asn Val Asn Leu Ala Ile Pro Ser Val Ser Ile Pro Phe
            340                 345                 350

Gly Glu Arg Phe Ile Thr Ile Leu Lys Ala Ser Gln Lys Asp Leu Val
        355                 360                 365

Asn Glu Phe Pro Gly Leu Phe Val Arg Gln Ser Arg Phe Ile Ala Gly
    370                 375                 380

Arg Pro Ser Arg Arg Asn Ile Arg Phe Lys Pro Trp Phe Ile Pro Gly
385                 390                 395                 400

Val Ile Asn Glu Ile Ser Leu Thr Asn Asn Glu Leu Tyr Ile Asn Asn
                405                 410                 415

Leu Phe Val Thr Pro Glu Ile His Asn Leu Phe Val Lys Arg Val Arg
            420                 425                 430

Phe Ser Leu Ile Arg Val His Lys Thr Gln Val Thr His Thr Asn Asn
        435                 440                 445
```

```
Asn His His Asp Glu Lys Leu Met Ser Ala Leu Lys Trp Pro Ile Glu
    450                 455                 460

Tyr Met Phe Ile Gly Leu Lys Pro Thr Trp Asn Ile Ser Asp Gln Pro
465                 470                 475                 480

Asn His Gln His Arg Asp Trp His Lys Phe Gly His Val Val Asn Ala
                485                 490                 495

Ile Met Gln Pro Thr His His Ala Glu Ile Ser Phe Gln Asp Arg Asp
            500                 505                 510

Thr Ala Leu Pro Asp Ala Cys Ser Ser Ile Ser Asp Ile Ser Pro Val
        515                 520                 525

Thr Tyr Pro Ile Thr Leu Pro Ile Ile Lys Asn Ile Ser Val Thr Ala
    530                 535                 540

His Gly Ile Asn Leu Ile Asp Lys Phe Pro Ser Lys Phe Cys Ser Ser
545                 550                 555                 560

Tyr Ile Pro Phe His Tyr Gly Gly Asn Ala Ile Lys Thr Pro Asp Asp
                565                 570                 575

Pro Gly Ala Met Met Ile Thr Phe Ala Leu Lys Pro Arg Glu Glu Tyr
            580                 585                 590

Gln Pro Ser Gly His Ile Asn Val Ser Arg Ala Arg Glu Phe Tyr Ile
        595                 600                 605

Ser Trp Asp Thr Asp Tyr Val Gly Ser Ile Thr Thr Ala Asp Leu Val
    610                 615                 620

Val Ser Ala Ser Ala Ile Asn Phe Leu Leu Leu Gln Asn Gly Ser Ala
625                 630                 635                 640

Val Leu Arg Tyr Ser Thr Lys Gly Glu Asn Leu Tyr Phe Gln Gly His
                645                 650                 655

His His His His His
            660
```

<210> SEQ ID NO 9
<211> LENGTH: 664
<212> TYPE: DNA
<213> ORGANISM: African swine fever virus

<400> SEQUENCE: 9

```
gaattcatgg attttatttt aaatatatcc atgaaaatgg aggtcatctt caaaacggat     60

ttaagatcat cttcacaagt tgtgtttcat gcgggtagcc tgtataattg gttttctgtt    120

gagattatca atagcggtag aattgttacg accgctataa aacattgct tagtactgtt    180

aagtatgata ttgtgaaatc tgctcgtata tatgcagggc aagggtatac tgaacatcag    240

gctcaagaag aatggaatat gattctgcat gtgctgtttg aagaggagac ggaatcctca    300

gcatcttcgg agaacattca tgaaaaaaat gataatgaaa ccaatgaatg cacatcctcc    360

tttgaaacgt tgtttgagca agagccctca tcggaggtac ctaaagactc caagctgtat    420

atgcttgcac aaaagactgt gcaacatatt gaacaatatg gaaaggcacc tgattttaac    480

aaggttatta gagcacataa ttttattcaa accatttatg gaacccctct aaaggaagaa    540

gaaaaagagg tggtaagact catggttatt aaacttttaa aaaaaataag cttttatctc    600

acctacatta aaggcgagaa cctgtatttt caaggccacc atcatcacca tcactagcgg    660

ccgc                                                                 664
```

<210> SEQ ID NO 10
<211> LENGTH: 216
<212> TYPE: PRT

-continued

<213> ORGANISM: African swine fever virus

<400> SEQUENCE: 10

```
Met Asp Phe Ile Leu Asn Ile Ser Met Lys Met Glu Val Ile Phe Lys
1               5                   10                  15

Thr Asp Leu Arg Ser Ser Ser Gln Val Val Phe His Ala Gly Ser Leu
            20                  25                  30

Tyr Asn Trp Phe Ser Val Glu Ile Ile Asn Ser Gly Arg Ile Val Thr
        35                  40                  45

Thr Ala Ile Lys Thr Leu Leu Ser Thr Val Lys Tyr Asp Ile Val Lys
    50                  55                  60

Ser Ala Arg Ile Tyr Ala Gly Gln Gly Tyr Thr Glu His Gln Ala Gln
65                  70                  75                  80

Glu Glu Trp Asn Met Ile Leu His Val Leu Phe Glu Glu Glu Thr Glu
                85                  90                  95

Ser Ser Ala Ser Ser Glu Asn Ile His Glu Lys Asn Asp Asn Glu Thr
            100                 105                 110

Asn Glu Cys Thr Ser Ser Phe Glu Thr Leu Phe Glu Gln Glu Pro Ser
        115                 120                 125

Ser Glu Val Pro Lys Asp Ser Lys Leu Tyr Met Leu Ala Gln Lys Thr
    130                 135                 140

Val Gln His Ile Glu Gln Tyr Gly Lys Ala Pro Asp Phe Asn Lys Val
145                 150                 155                 160

Ile Arg Ala His Asn Phe Ile Gln Thr Ile Tyr Gly Thr Pro Leu Lys
                165                 170                 175

Glu Glu Glu Lys Glu Val Val Arg Leu Met Val Ile Lys Leu Leu Lys
            180                 185                 190

Lys Ile Ser Phe Tyr Leu Thr Tyr Ile Lys Gly Glu Asn Leu Tyr Phe
        195                 200                 205

Gln Gly His His His His His His
    210                 215
```

<210> SEQ ID NO 11
<211> LENGTH: 613
<212> TYPE: DNA
<213> ORGANISM: African swine fever virus

<400> SEQUENCE: 11

```
gaattcatgg attctgaatt ttttcaaccg gtttatccgc ggcattatgg tgagtgtttg      60

tcaccagtca ctacaccaag cttcttctcc acacatatgt atactattct cattgctatc     120

gtggtcttag tcatcattat catcgttcta atctatctat tctcttcaag aaagaaaaaa     180

gctgctgcta ttgaggagga agatatacag tttataaatc cttatcaaga tcagcagtgg     240

gtagaagtca ctccacaacc aggtacctct aaaccagctg gagcgactac agcaagtgta     300

ggcaagccag tcacgggcag accggcaaca aacagaccag caacaaacaa accagttacg     360

gacaacccag ttacggacag actagtcatg gcaactggcg ggccggctgc tgcacctgca     420

gctgcgagtg ctcctgctca tccggctgag ccttacacga cagtcactac tcagaacact     480

gcttcacaaa caatgtcggc tattgaaaat ttacgacaaa gaaacaccta tacgcataaa     540

gacctagaaa actccttgaa aggcgagaac ctgtattttc aaggccacca tcatcaccat     600

cactagcggc cgc                                                        613
```

<210> SEQ ID NO 12
<211> LENGTH: 199

```
<212> TYPE: PRT
<213> ORGANISM: African swine fever virus

<400> SEQUENCE: 12

Met Asp Ser Glu Phe Phe Gln Pro Val Tyr Pro Arg His Tyr Gly Glu
1               5                   10                  15

Cys Leu Ser Pro Val Thr Thr Pro Ser Phe Phe Ser Thr His Met Tyr
            20                  25                  30

Thr Ile Leu Ile Ala Ile Val Val Leu Val Ile Ile Ile Ile Val Leu
        35                  40                  45

Ile Tyr Leu Phe Ser Ser Arg Lys Lys Lys Ala Ala Ala Ile Glu Glu
    50                  55                  60

Glu Asp Ile Gln Phe Ile Asn Pro Tyr Gln Asp Gln Gln Trp Val Glu
65                  70                  75                  80

Val Thr Pro Gln Pro Gly Thr Ser Lys Pro Ala Gly Ala Thr Thr Ala
                85                  90                  95

Ser Val Gly Lys Pro Val Thr Gly Arg Pro Ala Thr Asn Arg Pro Ala
            100                 105                 110

Thr Asn Lys Pro Val Thr Asp Asn Pro Val Thr Asp Arg Leu Val Met
        115                 120                 125

Ala Thr Gly Gly Pro Ala Ala Ala Pro Ala Ala Ala Ser Ala Pro Ala
    130                 135                 140

His Pro Ala Glu Pro Tyr Thr Thr Val Thr Thr Gln Asn Thr Ala Ser
145                 150                 155                 160

Gln Thr Met Ser Ala Ile Glu Asn Leu Arg Gln Arg Asn Thr Tyr Thr
                165                 170                 175

His Lys Asp Leu Glu Asn Ser Leu Lys Gly Glu Asn Leu Tyr Phe Gln
            180                 185                 190

Gly His His His His His His
        195


<210> SEQ ID NO 13
<211> LENGTH: 1083
<212> TYPE: DNA
<213> ORGANISM: African swine fever virus

<400> SEQUENCE: 13

atgataatac ttattttttt aatattttct aacatagttt taagtattga ttattgggtt      60

agttttaata aaacaataat tttagatagt aatattacta atgataataa tgatataaat     120

ggagtatcat ggaatttttt taataattct tttaatacac tagctacatg tggaaaagca     180

ggtaactttt gtgaatgttc taattatagt acatcaatat ataatataac aaataattgt     240

agcttaacta tttttcctca taatgatgta tttgatacaa catatcaagt agtatggaat     300

caaataatta attatacaat aaaattatta acacctgcta ctcccccaaa tatcacatat     360

aattgtacta attttttaat aacatgtaaa aaaaataatg gaacaaacac taatatatat     420

ttaaatataa atgatacttt tgttaaatat actaatgaaa gtatacttga atataactgg     480

aataatagta acattaacaa ttttacagct acatgtataa ttaataatac aattagtaca     540

tctaatgaaa caacacttat aaattgtact tatttaacat tgtcatctaa ctatttttat     600

acttttttta aattatatta tattccatta agcatcataa ttgggataac aataagtatt     660

cttcttatat ccatcataac ttttttatct ttacgaaaaa gaaaaaaaca tgttgaagaa     720

atagaaagtc caccacctga atctaatgaa gaagaacaat gtcagcatga tgacaccact     780

tccatacatg aaccatctcc cagagaacca ttacttccta agccttacag tcgttatcag     840
```

-continued tataatacac ctatttacta catgcgtccc tcaacacaac cactcaaccc atttccctta 900
cctaaaccgt gtcctccacc caaaccatgt ccgccaccca aaccatgtcc tccacctaaa 960
ccatgtcctt cagctgaatc ctattctcca cccaaaccac tacctagtat cccgctacta 1020
cccaatatcc cgccattatc tacccaaaat atttcgctta ttcacgtaga tagaattatt 1080
taa 1083

<210> SEQ ID NO 14
<211> LENGTH: 1160
<212> TYPE: DNA
<213> ORGANISM: African swine fever virus
<220> FEATURE:
<221> NAME/KEY: misc_feature
<222> LOCATION: (10)..(15)
<223> OTHER INFORMATION: EcoRI Restriction Site
<220> FEATURE:
<221> NAME/KEY: misc_feature
<222> LOCATION: (1096)..(1122)
<223> OTHER INFORMATION: TEV Restriction Site
<220> FEATURE:
<221> NAME/KEY: misc_feature
<222> LOCATION: (1123)..(1143)
<223> OTHER INFORMATION: HIS Tag + Stop Codon
<220> FEATURE:
<221> NAME/KEY: misc_feature
<222> LOCATION: (1151)..(1156)
<223> OTHER INFORMATION: NotI Restriction Site

<400> SEQUENCE: 14
ggacctaagg aattcatgat aattctgatc tttttgatat tcagtaatat cgtgttatcg 60
atagactact gggtgtcttt caataagact atcattttag actcaaacat taccaatgac 120
aacaacgata tcaatggagt ctcttggaat ttttttaaca acagtttcaa cactcttgca 180
acttgcggga aggctggtaa tttttgtgag tgtagcaact actccacgtc tatctataat 240
attacaaata actgttcatt gactattttt cctcataacg acgtattcga cacaacatac 300
caggtagtgt ggaatcaaat aataaattac actatcaaac ttctgacacc ggcgacgccc 360
cccaacatca catataattg tacgaatttc cttataacat gcaaaaagaa caacggtacc 420
aatactaata tctacctgaa catcaacgat accttcgtta aatatactaa tgagtcgatc 480
ttagagtaca actggaacaa ttctaatatt aacaatttta ctgccacttg tataataaat 540
aacactataa gtacgtccaa tgagaccacg cttatcaact gcacatattt gacactatct 600
tctaactatt tttatacgtt ttttaagttg tattatatcc ctctgtcaat catcataggg 660
ataacaatca gcatacttct catttcaatt atcacttttt taagccttcg taaacgcaag 720
aagcatgtgg aagaaataga atctcctccg ccggagagca atgaagagga acaatgtcag 780
catgacgata caacatcaat ccatgagcca tcgcctagag agccactgct gcccaaacct 840
tattcacgtt atcaatacaa tacgccaata tattacatgc gccctagcac acagccacta 900
aatccgtttc cgctgccgaa gccgtgtcca ccccctaagc cgtgcccacc gcctaaaccc 960
tgccctcctc ccaagccatg tccctcggca gagtcatatt ccccacctaa gcccttaccg 1020
tccatccctc tgctaccaaa tatacctccc ctgagtaccc aaaatatttc cttaatccat 1080
gtagaccgaa tcatcaaggg cgaaaacttg tactttcaag gccatcacca tcaccatcac 1140
taggcggccg caattgccaa 1160

<210> SEQ ID NO 15
<211> LENGTH: 20
<212> TYPE: DNA

<213> ORGANISM: Artificial Sequence
<220> FEATURE:
<223> OTHER INFORMATION: PCR Primer

<400> SEQUENCE: 15
cggcggagga gattctattt 20

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
tccaatgaga ccacgcttat c 21

<210> SEQ ID NO 17
<211> LENGTH: 375
<212> TYPE: PRT
<213> ORGANISM: African swine fever virus

<400> SEQUENCE: 17

```
Met Ile Ile Leu Ile Phe Leu Ile Phe Ser Asn Ile Val Leu Ser Ile
1               5                   10                  15

Asp Tyr Trp Val Ser Phe Asn Lys Thr Ile Ile Leu Asp Ser Asn Ile
            20                  25                  30

Thr Asn Asp Asn Asn Asp Ile Asn Gly Val Ser Trp Asn Phe Phe Asn
        35                  40                  45

Asn Ser Phe Asn Thr Leu Ala Thr Cys Gly Lys Ala Gly Asn Phe Cys
    50                  55                  60

Glu Cys Ser Asn Tyr Ser Thr Ser Ile Tyr Asn Ile Thr Asn Asn Cys
65                  70                  75                  80

Ser Leu Thr Ile Phe Pro His Asn Asp Val Phe Asp Thr Thr Tyr Gln
                85                  90                  95

Val Val Trp Asn Gln Ile Ile Asn Tyr Thr Ile Lys Leu Leu Thr Pro
            100                 105                 110

Ala Thr Pro Pro Asn Ile Thr Tyr Asn Cys Thr Asn Phe Leu Ile Thr
        115                 120                 125

Cys Lys Lys Asn Asn Gly Thr Asn Thr Asn Ile Tyr Leu Asn Ile Asn
    130                 135                 140

Asp Thr Phe Val Lys Tyr Thr Asn Glu Ser Ile Leu Glu Tyr Asn Trp
145                 150                 155                 160

Asn Asn Ser Asn Ile Asn Asn Phe Thr Ala Thr Cys Ile Ile Asn Asn
                165                 170                 175

Thr Ile Ser Thr Ser Asn Glu Thr Thr Leu Ile Asn Cys Thr Tyr Leu
            180                 185                 190

Thr Leu Ser Ser Asn Tyr Phe Tyr Thr Phe Phe Lys Leu Tyr Tyr Ile
        195                 200                 205

Pro Leu Ser Ile Ile Ile Gly Ile Thr Ile Ser Ile Leu Leu Ile Ser
    210                 215                 220

Ile Ile Thr Phe Leu Ser Leu Arg Lys Arg Lys Lys His Val Glu Glu
225                 230                 235                 240

Ile Glu Ser Pro Pro Pro Glu Ser Asn Glu Glu Glu Gln Cys Gln His
                245                 250                 255

Asp Asp Thr Thr Ser Ile His Glu Pro Ser Pro Arg Glu Pro Leu Leu
            260                 265                 270
```

-continued

```
Pro Lys Pro Tyr Ser Arg Tyr Gln Tyr Asn Thr Pro Ile Tyr Tyr Met
        275                 280                 285

Arg Pro Ser Thr Gln Pro Leu Asn Pro Phe Pro Leu Pro Lys Pro Cys
    290                 295                 300

Pro Pro Pro Lys Pro Cys Pro Pro Pro Lys Pro Cys Pro Pro Pro Lys
305                 310                 315                 320

Pro Cys Pro Ser Ala Glu Ser Tyr Ser Pro Pro Lys Pro Leu Pro Ser
                325                 330                 335

Ile Pro Leu Leu Pro Asn Ile Pro Pro Leu Ser Thr Gln Asn Ile Ser
            340                 345                 350

Leu Ile His Val Asp Arg Ile Ile Lys Gly Glu Asn Leu Tyr Phe Gln
        355                 360                 365

Gly His His His His His His
    370                 375
```

AFRICAN SWINE FEVER (ASF) VIRUS VACCINES

CROSS REFERENCE TO RELATED APPLICATION

This application claims benefit under 35 U.S.C. §119(e) to U.S. Provisional Application No.: 63/128,318, filed Dec. 21, 2020, which is incorporated by reference herein in its entirety.

Field of Invention

The present invention pertains generally to compositions that elicit immune responses against African Swine Fever (ASF) virus. In particular, the invention relates to immunogenic compositions (e.g., vaccines) comprising immunogenic polypeptides of ASF virus. Immunogenic compositions, in addition, may contain antigens other than ASF virus antigens. Methods of eliciting an immune response with the immunogenic compositions as disclosed herein and methods of treating an ASF infection are also described.

Background Information

African swine fever (ASF) is a viral disease of swine that leads to a high mortality in domestic pigs while being asymptomatic in the natural suid reservoir hosts. It causes important economic losses that are unavoidable in the absence of an effective vaccine and the available methods of disease control are the quarantine of the affected area and the slaughter of the infected animals. ASF is caused by the ASF virus (ASFV), a double-stranded DNA virus with a complex molecular structure. It is the only member of the Asfarviridae family and the only DNA virus transmitted by arthropods, soft ticks of the Ornithodoros genus. Soft ticks (Ornithodoros moubata) are involved in the sylvatic transmission cycle of the virus in Africa and O. erraticus in Europe. The wild boar that suffers an acute disease similar to the domestic pig appears to be relevant in the transmission cycle in Europe.

The disease caused by this virus was first identified in Kenya in the 1920s. Then, it was confined to Africa until it spread to Europe in the middle of the last century, and later to South America and the Caribbean. The disease was eradicated from Europe (except of Sardinia) at the 1990s via drastic control and eradication programs. However, in 2007, the disease spread again out of Africa into the Caucasus, especially Georgia, and in 2014 it reached the eastern territory of the European Union. The latest reports of the disease include an increasing list of EU countries, Poland and the three Baltic republics and very recently Moldova. Due to the absence of vaccines with protective efficacy, ASF represents a serious threat to all European countries. The epidemiological complexity of ASF has been clearly demonstrated in eastern and southern Africa, where genetic characterization of ASFV based on sequence variation in the C-terminal region of the B646L gene encoding the major capsid protein p72, revealed the presence of 22 genotypes. Recently, a new genotype, genotype XXIII, that shares a common ancestor with genotypes IX and X, which comprise isolates circulating in Eastern African countries and the Republic of Congo, has been described. This review paper summarizes the current state of knowledge about ASFV.

ASFV is a large, enveloped virus with icosahedral morphology and an average diameter of 200 nm. The viral genome consists of a single molecule of linear, covalently close-ended, double stranded DNA. The genomes of different isolates vary in length between 170 and 190 Kbp and encode between 151 and 167 open reading frames. ASFV replication cycle is mainly cytoplasmic, but the nucleus is also a site of viral DNA synthesis at early times. The disassembly of the lamina network close to the sites where the viral genome starts its replication and the redistribution of several nuclear proteins suggests the existence of sophisticated mechanisms to regulate the nuclear machinery during viral infection.

Transcription of viral genes is strongly regulated. Four classes of mRNAs have been identified by their distinctive accumulation kinetics—including immediate—early, early, intermediate, and late transcripts. Immediate—early and early genes are expressed before the onset of DNA replication, whereas intermediate and late genes are expressed afterwards. The presence of intermediate genes suggests a cascade model for the regulation of ASFV gene expression. Enzymes required for DNA replication are expressed immediately after virus entry into the cytoplasm from partially uncoated core particles and using enzymes and other factors packaged in virus particles. Virus morphogenesis takes place in the viral factories where the main late phase of DNA replication also occurs.

The ASFV particle has an icosahedral morphology composed of several concentric domains: the internal core formed by the central genome contains the nucleoid, which is coated by a thick protein layer named core shell; an inner lipid envelope surrounding the core; and finally, the capsid, which is the outermost layer of the intracellular virions. The extracellular virions possess an additional external envelope that is obtained when the virus buds out through the plasma membrane. However, the importance of this envelope is unclear as it is not required for infectivity.

The current approaches to ASF vaccines are largely broken down into two "camps." The current approach taken by the USDA and DHS focuses on modified live vaccines, believing that the replication of the virus inside cells is absolutely required to generate a protective response. However, the most advanced prototype vaccine that falls into this category was recently stated to be "at least 8 years out from licensing to use," and carries many safety concerns. Recent studies have demonstrated a highly effective gene-deleted ASF mutant vaccine weakly replicates in pigs, but provides protection from lethal challenge in vaccinated animals.

While promising, the use of live attenuated strain for the US vaccine is problematic, and culture of the vaccine virus currently requires the use of primary macrophages. There are colloquial reports of a Chinese attempt to duplicate the vaccine that resulted in negative outcomes, however this remains to be confirmed.

A second vaccine developed at Pirbright Laboratory in the UK has also shown promise, again protecting against lethal consequences of ASF infection but noy limiting viral replication. Briefly, this two dose vaccine was developed by combining 8 individual recombinant adenoviruses expressing 8 unique ASF proteins into a single vaccine. When administered, the results appear to be similar to that observed in earlier studies using fewer proteins.

In contrast to using the live approach, subunit vaccines are killed products; due to difficulties associated with delineating protective protein targets, and generating broadly-protective vaccines against multiple strains, these vaccines have largely been ignored.

Thus, there remains a need for an improved therapy for treating subjects presenting clinical symptoms associated with ASF virus infection and methods for preventing the spread of infection.

SUMMARY OF THE INVENTION

The present invention provides immunogenic compositions comprising African Swine Fever (ASF) virus antigens, in particular as a part of subunit vaccines.

In embodiments, methods for producing ASF virus-derived immunogenic polypeptides and/or peptides may be mixed or co-expressed with adjuvants are disclosed. Immunogenic compositions may include one or more polypeptides and/or adjuvants as described herein. For example, immunogenic compositions may comprise other antigens that may be used in immunization against pathogens that cause other diseases, such as antigens derived from non-ASF virus pathogens.

In embodiments, a process for producing a polypeptide is disclosed including the step of culturing a host cell transformed with a nucleic acid as described herein under conditions which induce polypeptide expression. In a related aspect, an ASF virus protein may be expressed by recombinant technology and used to develop an immunogenic composition comprising a recombinant antigenic subunit, where such expressed polypeptide is generated using baculovirus/insect cell methodology.

In one aspect, a process for producing nucleic acid is disclosed, where the nucleic acid encoding an ASF virus-derived protein or polypeptide is prepared (at least in part) by chemical synthesis. In a related aspect, the process includes amplifying nucleic acids using a primer-based amplification method (e.g., PCR).

In another aspect, a process for producing a protein complex is disclosed, including administering an ASF virus derived polypeptide, or a fragment thereof, to a subject. In a related aspect, the process includes admixing an ASF virus-derived polypeptide with a pharmaceutically acceptable carrier or diluent. In a further related aspect, the composition may include the polypeptide as set forth in SEQ ID NOs:6 (p30/p54 fusion protein), 8 (p72 protein), 10 (p30 protein), 12 (p54 protein), 17 (hemagglutinin protein). In a still further related aspect, the polypeptide composition includes SEQ ID NOs:6 and 17.

In embodiments, a method of eliciting an immunological response in a subject is disclosed including administering a composition of the instant disclosure. In a related aspect, the method further includes administering an adjuvant. In a further related aspect, the method includes administering the immunogenic composition to the subject via topical, parenteral or mucosal route.

In one aspect, the administration may be multiple administrations, where a first immunogenic composition and a second immunogenic composition are the same. In another aspect, the first immunogenic composition and the second immunogenic composition are different.

In one aspect, administration is performed two or more times.

In embodiments, a method for treating an infection by an ASF virus is disclosed including administering to a subject in need thereof a therapeutically effective amount of an immunogenic composition as described herein.

In one aspect, multiple therapeutically effective doses of the immunogenic composition are administered to a subject.

In a related aspect, the method includes mucosally administering a therapeutically effective amount of a first immunogenic composition comprising one or more ASF virus antigens and topically or parenterally administering a therapeutically effective amount of a second immunogenic composition comprising one or more ASF virus antigens.

In one aspect, multiple therapeutically effective doses of the immunogenic composition are administered to a subject. In another aspect, an immunogenic composition comprises a separate, non-ASF virus antigen.

In one aspect, the composition comprises an ASF virus p30/p54 fusion protein.

In a related aspect, the composition comprises an ASF virus hemagglutinin protein. In a further related aspect, the composition comprises administering a composition comprising ASF virus p30/p54 fusion protein and ASF virus hemagglutinin protein.

In one aspect, the subject is a pig. In a related aspect, the proteins are administered substantially simultaneously or sequentially.

These and other embodiments of the instant subject matter as disclosed will readily occur to those of skill in the art in view of the instant disclosure.

DETAILED DESCRIPTION OF THE INVENTION

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a," "an," and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein may be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will mean plus or minus <10% of particular term and "substantially" and "significantly" will mean plus or minus >10% of the particular term. In embodiments, compositions may "contain," "comprise" or "consist essentially of" a particular component or group of components, where the skilled artisan would understand the latter to mean the scope of the claim is limited to the specified materials or steps "and those that do not materially affect the basic and novel characteristic(s)" of the claimed invention.

As used herein, the term "ASF" refer to members of the genus Asfivirus of the family Asfarviridae of African. Swine Fever viruses. The term ASF includes strains in all genogroups of the virus. Currently, ASF strains are divided into 24 genogroups (Gx-Gxn) based on sequencing of their the p72/B646L gene. The term ASF also includes isolates not characterized at the time of filing.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation and the like. Furthermore, for purposes of the present disclosure, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises about 50%, about 80%-85%, or about 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism or cell with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used include fluorescein, rhodamine, dansyl, umbelliferone, Texas red, luminol, acradimum esters, NADPH and α-β-galactosidase.

"Homology" refers to the percent identity between two polynucleotide or two polypeptide moieties. Two nucleic acid, or two polypeptide sequences are "substantially homologous" to each other when the sequences exhibit at least about 50% sequence identity, at least about 75% sequence identity, at least about 80%-85% sequence identity, at least about 90% sequence identity, and at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity may be determined by a direct comparison of the sequence information between two molecules by aligning the sequences, counting the exact number of matches between the two aligned sequences, dividing by the length of the shorter sequence, and multiplying the result by 100. Readily available computer programs may be used to aid in the analysis, such as ALIGN, Dayhoff, M. O. in Atlas of Protein Sequence and Structure M. O. Dayhoff, ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence may be determined using the homology algorithm of Smith and Waterman with a default scoring table and a gap penalty of six nucleotide positions.

Another method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, CA) From this suite of packages the Smith-Waterman algorithm may be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology may be determined by hybridization of polynucleotides under conditions which form stable duplexes between homologous regions, followed by digestion with single-stranded-specific nuclease(s), and size determination of the digested fragments. DNA sequences that are substantially homologous may be identified in a Southern hybridization experiment under, for example, stringent conditions, as defined for that particular system. Defining appropriate hybridization conditions is within the skill of the art.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells," "host cells," "cells," "cell lines," "cell cultures," and other such terms denoting microorganisms or higher eukaryotic cell lines cultured as unicellular entities refer to cells which may be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence may be determined by a start codon at the 5' (amino) terminus and a translation stop codon at the 3' (carboxy) terminus. A coding sequence may include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

The term "nucleic acid" includes DNA and RNA, and also their analogues, such as those containing modified backbones (e.g., phosphorothioates, and the like), and also peptide nucleic acids (PNA), and the like. The present disclosure provides nucleic acids comprising sequences complementary to those described above (e.g., for antisense or probing purposes).

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences may be present between the promoter sequence and the coding sequence and the promoter sequence may still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, at least 8 to 10 amino acids, and at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. In embodiments, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, less than about 70%, and less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. Such techniques may be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which may transfer nucleic acid sequences to target cells. Thus, the term includes cloning and expression vehicles, as well as viral vectors.

By "fragment" is intended a molecule consisting of only a part of the intact full-length sequence and structure. A fragment of a polypeptide may include a C-terminal deletion, an N-terminal deletion, and/or an internal deletion of the native polypeptide. A fragment of a polypeptide will generally include at least about 5-10 contiguous amino acid residues of the full-length molecule, at least about 15-25 contiguous amino acid residues of the full-length molecule, and at least about 20-50 or more contiguous amino acid residues of the full-length molecule, or any integer between 5 amino acids and the number of amino acids in the full-length sequence, provided that the fragment in question retains the ability to elicit the desired biological response. A fragment of a nucleic acid may include a 5'-deletion, a 3'-deletion, and/or an internal deletion of a nucleic acid. Nucleic acid fragments will generally include at least about 5-1000 contiguous nucleotide bases of the full-length molecule and may include at least 5, 10, 15, 20, 25, 30, 40, 50, 60, 75, 100, 150, 250 or at least 500 contiguous nucleotides of the full-length molecule, or any integer between 5 nucleotides and the number of nucleotides in the full-length sequence. Such fragments may be useful in hybridization, amplification, production of immunogenic fragments, or nucleic acid immunization.

By "immunogenic fragment" is meant a fragment of an immunogen which includes one or more epitopes and thus may modulate an immune response or may act as an adjuvant for a co-administered antigen. Such fragments may be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871, incorporated herein by reference in its entirety. Similarly, conformational epitopes are readily identified by determining spatial conformation of amino acids such as by, e.g., x-ray crystallography and 2-dimensional nuclear magnetic resonance.

Immunogenic fragments, for purposes of the present disclosure, will usually be at least about 2 amino acids in length, about 5 amino acids in length, and at least about 10 to about 15 amino acids in length. There is no critical upper limit to the length of the fragment, which could comprise nearly the full-length of the protein sequence, or even a fusion protein comprising two or more epitopes.

As used herein, the term "epitope" generally refers to the site on an antigen which is recognized by a T-cell receptor and/or an antibody. In embodiments, it is a short peptide derived from or as part of a protein antigen. However, the term is also intended to include peptides with glycopeptides and carbohydrate epitopes. Several different epitopes may be carried by a single antigenic molecule. The term "epitope" also includes modified sequences of amino acids or carbohydrates which stimulate responses which recognize the whole organism. It is advantageous if the selected epitope is an epitope of an infectious agent, which agent causes the infectious disease.

The epitope may be generated from knowledge of the amino acid and corresponding DNA sequences of the peptide or polypeptide, as well as from the nature of particular amino acids (e.g., size, charge, and the like) and the codon dictionary, without undue experimentation. Some guidelines in determining whether a protein will stimulate a response, include: Peptide length—the peptide is about 8 or 9 amino acids long to fit into the MHC class I complex and about 13-25 amino acids long to fit into a class II MHC complex. This length is a minimum for the peptide to bind to the MHC complex. In one aspect, the peptides may be longer than these lengths because cells may cut peptides. The peptide may contain an appropriate anchor motif which will enable it to bind to the various class I or class II molecules with high enough specificity to generate an immune response. This may be done, without undue experimentation, by comparing the sequence of the protein of interest with published structures of peptides associated with the MHC molecules. Thus, the skilled artisan may ascertain an epitope of interest by comparing the protein sequence with sequences listed in the protein database.

As used herein, the term "T cell epitope" refers generally to those features of a peptide structure which are capable of inducing a T cell response and a "B cell epitope" refers generally to those features of a peptide structure which are capable of inducing a B cell response.

An "immunological response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes may be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. Recent methods of measuring cell-mediated immune response include measurement of intracellular cytokines or cytokine secretion by T-cell populations, or by measurement of epitope specific T-cells.

Thus, an immunological response as used herein may be one that stimulates the production of antibodies (e.g., neutralizing antibodies that block bacterial toxins and pathogens such as viruses entering cells and replicating by binding to toxins and pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses may be determined using standard immunoassays and neutralization assays, well known in the art. The innate immune system of mammals also recognizes and responds to molecular features of pathogenic organisms via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature Dendritic cells of the monocyte and plamsacytoid lineage (MDC, PDC), as well as gamma, delta, alpha and beta T cells and B cells and the like. Thus, the present disclosure also contemplates an immune response wherein the immune response involves both an innate and adaptive response.

An "immunogenic composition" is a composition that comprises an antigenic molecule where administration of the composition to a subject results in the development in the subject of a humoral and/or a cellular immune response to the antigenic molecule of interest.

The terms "immunogenic" protein or polypeptide refer to an amino acid sequence which elicits an immunological response as described above. An "immunogenic" protein or polypeptide, as used herein, includes the full-length sequence of the protein in question, including the precursor and mature forms, analogs thereof, or immunogenic fragments thereof.

"Gene transfer" or "gene delivery" refers to methods or systems for reliably inserting DNA or RNA of interest into a host cell. Such methods may result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses. When used for immunization, such gene delivery expression vectors may be referred to as vaccines or vaccine vectors.

The term "derived from" is used herein to identify the original source of a molecule but is not meant to limit the method by which the molecule is made which may be, for example, by chemical synthesis or recombinant means.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

A polynucleotide "derived from" a designated sequence refers to a polynucleotide sequence which comprises a contiguous sequence of approximately at least about 6 nucleotides, at least about 8 nucleotides, at least about 10-12 nucleotides, and at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

An ASF polynucleotide, oligonucleotide, nucleic acid, protein, polypeptide, or peptide, as defined above, is a molecule derived from an ASF virus, including, without limitation, any of the various isolates of ASF virus. The molecule need not be physically derived from the particular isolate in question, but may be synthetically or recombinantly produced.

The genomic DNA consists of 168 open reading frames (ORF). Some of these proteins derive from larger precursors that result from further post-translational modifications of the precursor proteins. In particular p30, p54, p72 and hemagglutinin polypeptides encoded by ASF virus ORFs, as well as variants thereof, immunogenic fragments thereof, and nucleic acids encoding such polypeptides, variants or immunogenic fragments may be used in the practice of the subject matter as disclosed.

Nucleic acid and protein sequences of interest for a number of ASF virus isolates are also known. Representative p30, p54, p'72, and hemagglutinin nucleic acid sequences are presented in SEQ ID NOs:1 (p30/p54 fusion), 7 (p'72), 9 (p30), 11 (p54), 13 (hemagglutinin) and 14 (hemagglutinin). Representative p30, p54, p'72, and hemagglutinin amino acid sequences are presented in SEQ ID NOs:6 (p30/p54 fusion), 8 (p'72), 10 (p30), 12 (p54), and 17 (hemagglutinin). Additional representative sequences, including sequences of ASF virus, and their encoded polypeptides from ASF virus isolates are listed in the National Center for Biotechnology Information (NCBI) database. See, for example, but not limited to, GenBank entries: CBw46759.1; ACJ61575.1; MH735140.1; MH601419.1; MH727102.1; KF834194.1; LC322015.1; MH735142; MH681419.1; KM609342.1; FR682468.1; KJ380910.1; FR682468.1; WH722357; MH68419.1; MH1713612.1; LC322016.1; KF834193.1 all of which sequences (as entered by the date of filing of this application) are herein incorporated by reference.

As used herein, the terms "p30" "p54" "p72" or "hemagglutinin" in reference to a AFS virus polypeptide refer to polypeptide scomprising a sequence homologous or identical to the "p30" "p54" "p72" or "hemagglutinin" polypeptides of an ASF virus, and include sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto. The capsid polypeptide may be encoded by either the same strain of ASF virus or in different strains of ASF virus.

As used herein, the term "p30/p54 fusion protein" refers to a protein comprising a sequence homologous or identical to the p30 ASF virus-encoded p30 and p54 proteins derived from an ASF virus, and includes sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but may be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which may mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules and any functional fragments obtained from such molecules, wherein such fragments retain specific-binding properties of the parent antibody molecule.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. In particular, ASF virus may be obtained from biological samples including, but not limited to, blood, serum, spleen, liver, lung, lymph nodes, tonsils, and kidney.

By "subject" is meant any member of the family suidae, including, without limitation, sus domesticus. The term does not denote a particular age. Thus, both adult and newborn individuals are intended to be covered.

The terms "variant," "analog" and "mutein" refer to biologically active derivatives of the reference molecule that retain desired activity, such as antigenic activity in inducing an immune response against ASF. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, and the like), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301). In embodiments, the analog or mutein has at least the same antigenic activity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that may tolerate change by reference to Hopp/Woods and Kyte-Doolittle plots, well known in the art.

The term "multiple epitope fusion antigen" or "multiple epitope fusion protein" as used herein intends a polypeptide in which multiple ASF virus antigens are part of a single, continuous chain of amino acids, which chain does not occur in nature. The ASF virus antigens may be connected directly to each other by peptide bonds or may be separated by intervening amino acid sequences. The fusion antigens may contain p30/p54 ASF virus-encoded polypeptides or fragments thereof. The fusion antigens may also contain sequences exogenous to the ASF virus. Moreover, the sequences present may be from multiple genotypes and/or isolates of ASF virus.

By "therapeutically effective amount" in the context of the immunogenic compositions is meant an amount of an immunogen (e.g., immunogenic polypeptide, fusion protein, polyprotein, or nucleic acid encoding an antigen) which will induce an immunological response, either for antibody production or for treatment or prevention of ASF infection. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γ, δ-T cell populations.

For purposes of the present disclosure, an "effective amount" of an adjuvant will be that amount which enhances an immunological response to a co-administered antigen or nucleic acid encoding an antigen.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

Before describing the present disclosure in detail, it is to be understood that the practice of the present disclosure will employ, unless otherwise indicated, conventional methods of virology, microbiology, molecular biology, recombinant DNA techniques and immunology all of which are within the ordinary skill of the art. Such techniques are explained fully in the literature. Although a number of methods and materials similar or equivalent to those described herein may be used in the practice of the present invention as claimed, the materials and methods are described herein.

The present disclosure includes compositions and methods for immunizing a subject against ASF infection. The instant disclosure provides immunogenic compositions comprising nucleic acids encoding capsid proteins and/or other immunogenic polypeptides from one or more strains of ASf virus, compositions comprising immunogenic polypeptides derived from one or more strains of ASFvirus. Immunogenic polypeptides to be used in the practice of the instant subject matter may include ASf virus-derived polypeptides, including multiple epitope fusion antigens. In addition, immunogenic compositions may comprise one or more adjuvants or nucleic acids encoding adjuvants, wherein immunogenic polypeptides are mixed or co-expressed with adjuvants. Immunogenic compositions may also comprise additional antigens other than ASF virus antigens, such as antigens that may be used in immunization against pathogens that cause diarrheal diseases.

In order to further an understanding of the subject matter as disclosed, a more detailed discussion is provided below regarding the production of nucleic acids and polypeptides for use in immunogenic compositions and methods of using such compositions in the treatment or prevention of ASF infection.

Structural Polypeptides, Nonstructural Polypeptides, and Polyproteins

The immunogenic compositions described herein may comprise one or more polypeptides derived from one or more genotypes and/or isolates of ASF virus. Polypeptides that may be used in the practice of the subject matter as disclosed herein include structural proteins, nonstructural proteins, and polyproteins. Such polypeptides may be full-length proteins or variants or immunogenic fragments thereof capable of eliciting an immune response to an ASF virus.

The polypeptides in immunogenic compositions may be encoded by any region of a ASF virus genome. Multiple polypeptides may be included in immunogenic compositions. Such compositions may comprise polypeptides from the same ASF virus isolate or from different strains and isolates, including isolates having any of the various ASF virus genotypes, to provide increased protection against a broad range of ASF virus genotypes. Multiple viral strains of ASF virus are known, and multiple polypeptides comprising epitopes derived from any of these strains may be used in immunogenic compositions.

The antigens used in the immunogenic compositions of the present disclosure may be present in the composition as individual separate polypeptides. Generally, the recombinant proteins of the present disclosure are expressed as a GST-fusion protein and/or a His-tagged fusion protein.

Multiepitope Fusion Proteins

The immunogenic compositions described herein may also comprise multiple epitope fusion proteins. Such fusion proteins include multiple epitopes derived from two or more viral polypeptides of one or more genotypes and/or isolates of ASF virus. Multiple epitope fusion proteins offer two principal advantages: first, a polypeptide that may be unstable or poorly expressed on its own may be assisted by adding a suitable hybrid partner that overcomes the problem; second, commercial manufacture is simplified as only one expression and purification need be employed in order to produce two polypeptides which are both antigenically useful.

The polypeptides in fusion proteins may be derived from the same ASF virus isolate or from different strains and isolates, including isolates having any of the various ASF virus genotypes, to provide increased protection against a broad range of virus genotypes. Multiple viral strains of ASF virus are known, and epitopes derived from any of these strains may be used in a fusion protein.

It is well known that any given species of organism varies from one individual organism to another and further that a given organism such as a virus may have a number of different strains. For example, as explained above, ASF virus includes at least 24 genogroups. In general, antigenic determinants may have a high degree of homology in terms of amino acid sequence, which degree of homology is generally 30% or more, 40% or more, when aligned. A fusion protein may also comprise multiple copies of an epitope, wherein one or more polypeptides of the fusion protein comprise sequences comprising exact copies of the same epitope. Additionally, polypeptides may be selected based on the particular viral clades endemic in specific geographic regions where vaccine compositions containing the fusions will be used. It is readily apparent that the subject fusions provide an effective means of treating ______ infection in a wide variety of contexts.

Multiple epitope fusion antigens may be represented by the formula $NH_2$-A-{-X-L-}$_n$-B—COOH, wherein: X is an amino acid sequence of an ASF virus antigen or a fragment thereof; L is an optional linker amino acid sequence; A is an optional N-terminal amino acid sequence; B is an optional C-terminal amino acid sequence; and n is 2, 3, 4, 5, 6, 7, 8, 9, 10, 11, 12, 13, 14 or 15.

If an —X— moiety has a leader peptide sequence in its wild-type form, this may be included or omitted in the multiple epitope fusion antigen. In some embodiments, the leader peptides will be deleted except for that of the —X— moiety located at the N-terminus of the hybrid protein i.e., the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of (—X-L-), linker amino acid sequence -L- may be present or absent. For instance, when n=2 the hybrid may be $NH_2$—$X_1$—$L_1$—$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, and the like. Linker amino acid sequence(s)-L- will typically be short, e.g., 20 or fewer amino acids (i.e., 20, 19, 18, 17, 16, 15, 14, 13, 12, 11, 10, 9, 8, 7, 6, 5, 4, 3, 2, 1). Examples include short peptide sequences which facilitate cloning, poly-glycine linkers (Gly, where n=2, 3, 4, 5, 6, 7, 8, 9, 10 or more), and histidine tags (His$_n$ where n=3, 4, 5, 6, 7, 8, 9, 10 or more). Other suitable linker amino acid sequences will be apparent to those skilled in the art. A useful linker is GSGGGG, with the Gly-Ser dipeptide being formed from a BamHI restriction site, which aids cloning and manipulation, and the $(Gly)_4$ tetrapeptide being a typical poly-glycine linker. In addition, protease substrate sequences may also be added (e.g., TEV protease: ENLYFQG).

-A- is an optional N-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking or short peptide sequences which facilitate cloning or purification (e.g., a histidine tag His$_n$ where n=3, 4, 5, 6, 7, 8, 9, 10 or more). Other suitable N-terminal amino acid sequences will be apparent to those skilled in the art. If $X_1$ lacks its own N-terminus methionine, -A- is an oligopeptide (e.g., with 1, 2, 3, 4, 5, 6, 7 or 8 amino acids) which provides a N-terminus methionine.

—B— is an optional C-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g., His$_n$ where n=3, 4, 5, 6, 7, 8, 9, 10 or more), or sequences which enhance protein stability. Other suitable C-terminal amino acid sequences will be apparent to those skilled in the art, including that such His, sequences may be removed when a TEV protease substrate sequence precedes it (e.g., ENLYFQGHis$_n$).

The individual antigens of the immunogenic composition within the multiple epitope fusion antigen (individual —X— moieties) may be from one or more strains or from one or more M types. Where n=2, for instance, $X_2$ may be from the same strain or type as $X_1$ or from a different strain or type. Where n=3, the strains might be (i) $X_1$=$X_2$=$X_3$, (ii) $X_1$=$X_2$ not equal to $X_3$, (iii) $X_1$ not equal to $X_2$=$X_3$, (iv) $X_1$ not equal to $X_2$ not equal to $X_3$, or (v) $X_1$=$X_3$ not equal to $X_3$, and the like.

Where multiple epitope fusion antigens are used, the individual antigens within the fusion protein (i.e., individual —X— moieties) may be from one or more strains. Where n=2, for instance, $X_2$ may be from the same strain as $X_1$ or from a different strain. Where n=3, the strains might be (i) $X_1$=$X_2$=$X_3$ (ii) $X_1$=$X_2$ not equal to $X_3$ (iii) $X_1$ not equal to $X_2$=$X_3$ (iv) $X_1$ not equal to $X_2$ not equal to $X_3$ or (v) $X_1$=$X_3$ not equal to $X_2$, and the like.

Accordingly, in embodiments, antigenic determinants from different ASF virus strains may be present. Representative multiepitope fusion proteins for use in the present disclosure, comprising polypeptides derived from ASF virus isolates, are discussed below. However, it is to be understood that multiepitope fusion proteins comprising other epitopes derived from ASF virus genomes or multiepitope fusion proteins comprising different arrangements of epitopes will also find use in immunogenic compositions as disclosed.

In certain embodiments, the fusion protein comprises one or more capsid and/or minor structural polypeptides from one or more isolates of ASF virus.

In another embodiment, the fusion protein comprises ASF virus polypeptides from more than one viral strain.

In all fusions described herein, the viral regions need not be in the order in which they occur naturally. Moreover, each of the regions may be derived from the same or different ASF virus isolates. The various ASF virus polypeptides present in the various fusions described above may either be full-length polypeptides or portions thereof.

If desired, the fusion proteins, or the individual components of these proteins, also may contain other amino acid sequences, such as amino acid linkers or signal sequences, as well as ligands useful in protein purification, such as glutathione-S-transferase and staphylococcal protein A.

Nucleic Acids

Nucleic acids for use as disclosed herein, for example, in polypeptide production, may be derived from any of the various regions of an ASF virus genomes.

Representative sequences from the ASF virus are known, including SEQ ID NOs:1, 7, 9, 11, 13 and 14.

Any of these sequences, as well as fragments and variants thereof that may be used in nucleic acid immunization to elicit an immune response to an ASF virus will find use in the present methods. Thus, the present disclosure provides variants of the above sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto. The present disclosure also provides polynucleotides encoding immunogenic fragments of an ASF virus polypeptide derived from any of the above sequences or a variant thereof. Polynucleotides may also comprise coding sequences for polypeptides which occur naturally or may be artificial sequences which do not occur in nature.

Polynucleotides may contain less than an entire ASF viral genome, or alternatively may include the sequence of an entire viral genomic DNA.

In embodiments, polynucleotides comprise one or more ASF viral sequences coding for the p30, p54, p72 and/or hemaagglutinin proteins of one or more isolates of ASF virus.

In embodiments, the present disclosure provides polynucleotides encoding a multiepitope fusion protein as described herein. Multiepitope fusion proteins may comprise sequences from one or more genotypes and/or isolates of ASF virus.

Nucleic acids according to the instant disclosure may be prepared in many ways (e.g., by chemical synthesis, from genomic or cDNA libraries, from the organism itself, etc.) and may take various forms (e.g., single stranded, double stranded, vectors, probes, and the like). In embodiments, nucleic acids are prepared in substantially pure form (i.e., substantially free from other host cell or non-host cell nucleic acids).

For example, nucleic acids may be obtained by screening cDNA and/or genomic libraries from cells infected with virus, or by deriving the gene from a vector known to include the same. For example, polynucleotides of interest may be isolated from a genomic library derived from viral DNA, present in, for example, hair or blood samples from an infected individual. Alternatively, ASF virus nucleic acids may be isolated from infected mammals or from biological samples collected from infected individuals. An amplification method such as PCR may be used to amplify polynucleotides from either ASF virus genomic DNA encoding therefor. Alternatively, polynucleotides may be synthesized in the laboratory, for example, using an automatic synthesizer. The nucleotide sequence may be designed with the appropriate codons for the particular amino acid sequence desired. In general, one will select preferred codons for the intended host in which the sequence will be expressed. The complete sequence of the polynucleotide of interest may be assembled from overlapping oligonucleotides prepared by standard methods and assembled into a complete coding sequence. The polynucleotides may be RNA or single- or double-stranded DNA. In embodiments, the polynucleotides are isolated free of other components, such as proteins and lipids.

Thus, particular nucleotide sequences may be obtained from vectors harboring the desired sequences or synthesized completely or in part using various oligonucleotide synthesis techniques known in the art, such as site-directed mutagenesis and polymerase chain reaction (PCR) techniques where appropriate. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. Primer sequences may include, but are not limited to, SEQ ID NOs: 2, 3, 4, 5, 15 and 16.

Production of Immunogenic Polypeptides

Polypeptides described herein may be prepared in any suitable manner (e.g., recombinant expression, purification from cell culture, chemical synthesis, and the like) and in various forms (e.g., native, fusions, non-glycosylated, lipidated, and the like). Such polypeptides include naturally-occurring polypeptides, recombinantly produced polypeptides, synthetically produced polypeptides, or polypeptides produced by a combination of these methods. Means for preparing such polypeptides are well understood in the art.

Polypeptides are prepared in substantially pure form (i.e., substantially free from other host cell or non-host cell proteins).

Polypeptides may be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid may then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These may include divinylbenzene cross-linked-styrene-based polymers, for example, divinylbenzene-hydroxymethylstyrene copolymers, divinylbenzene-chloromethyl styrene copolymers and divinylbenzene-benzhydrylaminopolystyrene copolymers.

The polypeptides of the present disclosure may also be chemically prepared by other methods such as by the method of simultaneous multiple peptide synthesis.

Alternatively, the above-described immunogenic polypeptides, polyproteins, and multiepitope fusion proteins may be produced recombinantly. Once coding sequences for the desired proteins have been isolated or synthesized, they may be cloned into any suitable vector or replicon for expression. Numerous cloning vectors are known to those of skill in the art, and the selection of an appropriate cloning vector is a matter of choice. A variety of bacterial, yeast, plant, mammalian and insect expression systems are available in the art and any such expression system may be used. Optionally, a polynucleotide encoding these proteins may be translated in a cell-free translation system. Such methods are well known in the art.

Examples of recombinant DNA vectors for cloning and host cells which they may xtransform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells).

Insect cell expression systems, such as baculovirus systems, may also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego, CA ("MaxBac" kit).

Plant expression systems may also be used to produce the immunogenic proteins. Generally, such systems use virus-based vectors to transfect plant cells with heterologous genes.

Viral systems, such as a vaccinia based infection/transfection system, will also find use with the subject matter as disclosed herein. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene may be placed under the control of a promoter, ribosome binding site (for bacterial expression) and, optionally, an operator (collectively referred to herein as "control" elements), so that the DNA sequence encoding the desired immunogenic polypeptide is transcribed into RNA in the host cell transformed by a vector containing this expression construction. The coding sequence may or may not contain a signal peptide or leader sequence. With the present subject matter as disclosed herein, both the naturally occurring signal peptides or heterologous sequences may be used. Leader sequences may be removed by the host in post-translational processing. See, e.g., U.S. Pat. Nos. 4,431,739; 4,425,437; 4,338,397, each herein incorporated by reference in their entireties. Such sequences include, but are not limited to, the tpa leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence may be cloned directly into an expression vector which already contains the control sequences and an appropriate restriction site.

In embodiments, it may be necessary to modify the coding sequence so that it may be attached to the control sequences with the appropriate orientation; i.e., to maintain the proper reading frame. It may also be desirable to produce mutants or analogs of the immunogenic polypeptides. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli, Bacillus subtilis,* and *Streptococcus* spp., will find use with the present expression constructs. Yeast hosts useful with the subject matter as disclosed include, inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica.* Insect cells for use with baculovirus expression vectors include, inter alia, *Aedes aegypti, Autographa californica, Bombyx mori, Drosophila melanogaster, Spodoptera frugiperda,* and *Trichoplusia ni.*

Depending on the expression system and host selected, the proteins as disclosed herein are produced by growing host cells transformed by an expression vector described above under conditions whereby the protein of interest is expressed. The selection of the appropriate growth conditions is within the skill of the art. The cells are then disrupted, using chemical, physical or mechanical means, which lyse the cells yet keep the ASF virus immunogenic polypeptides substantially intact. Intracellular proteins may also be obtained by removing components from the cell wall or membrane, e.g., by the use of detergents or organic solvents, such that leakage of the immunogenic polypeptides occurs.

For example, methods of disrupting cells for use with the subject matter as disclosed herein include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced ASF virus immunogenic polypeptides are further purified, using standard purification techniques such as but not limited to, column chromatography, ion-exchange chromatography, size-exclusion chromatography, electrophoresis, HPLC, immunoabsorbent techniques, affinity chromatography, immunoprecipitation, and the like.

For example, one method for obtaining the intracellular ASF virus immunogenic polypeptides as disclosed herein involves affinity purification, such as by immunoaffinity chromatography using specific antibodies. The choice of a suitable affinity resin is within the skill in the art. After affinity purification, immunogenic polypeptides may be further purified using conventional techniques well known in the art, such as by any of the techniques described above.

It may be desirable to produce multiple polypeptides simultaneously (e.g., structural and/or nonstructural proteins from one or more viral strains or viral polypeptides in combination with polypeptide adjuvants). Production of two or more different polypeptides may readily be accomplished by e.g., co-transfecting host cells with constructs encoding the different polypeptides. Co-transfection may be accomplished either in trans or cis, i.e., by using separate vectors or by using a single vector encoding the polypeptides. If a single vector is used, expression of the polypeptides may be driven by a single set of control elements or, alternatively, the sequences coding for the polypeptides may be present on the vector in individual expression cassettes, regulated by individual control elements.

The polypeptides described herein may be attached to a solid support. The solid supports which may be used in the practice with the subject matter as disclosed herein include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more ASF viral antigens) under suitable binding conditions such that the component is sufficiently immobilized to the support. Sometimes, immobilization of the antigen to the support may be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that may be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art.

If desired, polypeptides may be labeled using conventional techniques. Suitable labels include fluorophores, chromophores, radioactive atoms (particularly $^{32}P$ and $^{125}I$, electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. “Specific binding partner” refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. A single label or a combination of labels may be used in the as disclosed herein.

Once formulated, the compositions as disclosed herein may be administered directly to the subject (e.g., as described above) or, alternatively, delivered ex vivo, to cells derived from the subject, using methods such as those described above.

Immunogenic Compositions

The present disclosure also provides compositions comprising one or more of the immunogenic polypeptides and/or polyproteins multiepitope fusion proteins described herein. Different polypeptides, polyproteins, and multiple epitope fusion proteins may be mixed together in a single formulation. Within such combinations, an antigen of the immunogenic composition may be present in more than one polypeptide, or multiple epitope polypeptide, or polyprotein.

The immunogenic compositions may comprise a mixture of polypeptides, which in turn may be delivered using the same or different vehicles. Antigens may be administered individually or in combination, in e.g., prophylactic (i.e., to prevent infection) or therapeutic (to treat infection) immunogenic compositions. The immunogenic composition may be given more than once (e.g., a “prime” administration followed by one or more “boosts”) to achieve the desired effects. The same composition may be administered in one or more priming and one or more boosting steps. Alternatively, different compositions may be used for priming and boosting.

The immunogenic compositions will generally include one or more "pharmaceutically acceptable excipients or vehicles" such as water, saline, glycerol, ethanol, and the like. Additionally, auxiliary substances, such as wetting or emulsifying agents, pH buffering substances, and the like, may be present in such vehicles.

Immunogenic compositions will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, and the like. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472.

Pharmaceutically acceptable salts may also be used in compositions as disclosed herein, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions as disclosed may also contain liquids or excipients, such as water, saline, glycerol, dextrose, ethanol, or the like, singly or in combination, as well as substances such as wetting agents, emulsifying agents, or pH buffering agents. Antigens may also be adsorbed to, entrapped within or otherwise associated with liposomes and particulate carriers such as PLG.

Antigens may be conjugated to a carrier protein in order to enhance immunogenicity. This is particularly useful in compositions in which a saccharide or carbohydrate antigen is used.

Carrier proteins may include, but are not limited to, bacterial toxins or toxoids, such as diphtheria or tetanus toxoids. The $CRM_{197}$ diphtheria toxoid may be used. Other carrier polypeptides include the N. meningitidis outer membrane protein (EP-A-0372501), synthetic peptides (EP-A-0378881 and EP-A-0427347), heat shock proteins (WO 93/17712 and WO 94/03208), pertussis proteins (WO 98/58668 and EP-A-0471177), protein D from H. influenzae (WO 00/56360), cytokines (WO 91/01146), lymphokines, hormones, growth factors, toxin A or B from C. difficile (WO 00/61761), iron-uptake proteins, such as transferring (WO 01/72337), etc. Where a mixture comprises capsular saccharide from both serigraphs A and C, it may be that the ratio (w/w) of MenA saccharide:MenC saccharide is greater than 1 (e.g., 2:1, 3:1, 4:1, 5:1, 10:1 or higher). Different saccharides may be conjugated to the same or different type of carrier protein. Any suitable conjugation reaction may be used, with any suitable linker where necessary.

Immunogenic compositions, including vaccines as disclosed may be administered in conjunction with other immunoregulatory agents. For example, a vaccine as disclosed herein may include an adjuvant. Adjuvants include, but are not limited to, one or more of the following types of adjuvants described below.

Mineral Containing Compositions

Mineral containing compositions suitable for use as adjuvants disclosed herein include mineral salts, such as aluminum salts and calcium salts. Salts as disclosed herein includes mineral salts such as hydroxides (e.g., oxyhydroxides), phosphates (e.g., hydroxyphosphates, orthophosphates), sulfates, and the like, or mixtures of different mineral compounds (e.g., a mixture of a phosphate and a hydroxide adjuvant, optionally with an excess of the phosphate), with the compounds taking any suitable form (e.g., gel, crystalline, amorphous, and the like). The mineral containing compositions may also be formulated as a particle of metal salt (WO00/23105).

Aluminum salts may be included in vaccines such that the dose of $Al^+$ is between 0.2 and 1.0 mg per dose.

In embodiments, the aluminum based adjuvant for use as disclosed is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. Alternatively, aluminum phosphate adjuvant ($AlPO_4$) or aluminum hydroxyphosphate, which contains phosphate groups in place of some or all of the hydroxyl groups of aluminum hydroxide adjuvant is provided. In embodiments, aluminum phosphate adjuvants provided herein are amorphous and soluble in acidic, basic and neutral media.

In embodiments, the adjuvant as disclosed herein comprises both aluminum phosphate and aluminum hydroxide. In one aspect, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (i.e., 11.4). Alternatively, pretreatment of aluminum hydroxide with phosphate lowers its isoelectric point, making it a preferred adjuvant for more basic antigens.

Oil-Emulsions

Oil-emulsion compositions suitable for use as adjuvants may include squalene-water emulsions, such as MF59 (5% Squalene, 0.5% TWEEN 80™, and 0.5% SPAN 85™, formulated into submicron particles using a microfluidizer). See WO90/14837. MF59 is used as the adjuvant in the FLUAD™ influenza virus trivalent subunit vaccine.

Particularly adjuvants for use in the compositions are submicron oil-in-water emulsions. Submicron oil-in-water emulsions for use herein may be squalene/water emulsions optionally containing varying amounts of MTP-PE, such as a submicron oil-in-water emulsion containing 4-5% w/v squalene, 0.25-1.0% w/v TWEEN 80™ (polyoxyelthylene-sorbitan monooleate), and/or 0.25-1.0% SPAN 85™ (sorbitan trioleate), and, optionally, N-acetylmuramyl-L-alanyl-D-isogluatminyl-L-alanine-2-(.beta.-2'-dipalmito- yl-sn-glycero-3-huydroxyphosphosphoryloxy)-ethylamine (MTP-PE), for example, the submicron oil-in-water emulsion known as "MF59" (International Publication No. WO90/14837; U.S. Pat. Nos. 6,299,884 and 6,451,325.) MF59 contains 4-5% w/v Squalene (e.g., 4.3%), 0.25-0.5% w/v TWEEN 80™, and 0.5% w/v SPAN 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, 0-250 μg/dose and 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 .mu.g MTP-PE per dose, and so on. MF69, another submicron oil-in-water emulsion for use herein, contains 4.3% w/v squalene, 0.25% w/v TWEEN 80™, and 0.75% w/v SPAN 85™ and optionally MTP-PE. Yet another submicron oil-in-water emulsion is MF75, also known as SAF, containing 10% squalene, 0.4% TWEEN 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants.

Saponin Formulations

Saponin formulations, may also be used as adjuvants. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins may also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. In embodiments, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols may be used to form unique particles called Immunostimulating Complexes (ISCOMs). ISCOMs typically also include a phospholipid such as phosphatidylethanolamine or phosphatidylcholine. Any known saponin may be used in ISCOMs. In embodiments, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

Bacterial or Microbial Derivatives

Adjuvants suitable for use as disclosed herein include bacterial or microbial derivatives such as:

(1) Non-Toxic Derivatives of Enterobacterial Lipopolysaccharide (LPs)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. One "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g., RC-529.

(2) Lipid A Derivatives

Lipid A derivatives include derivatives of lipid A from Escherichia coli such as OM-174.

(3) Immunostimulatory Oligonucleotides

Immunostimulatory oligonucleotides suitable for use as adjuvants may include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's may include nucleotide modifications/analogs such as phosphorothioate modifications and may be double-stranded or single-stranded. Optionally, the guanosine may be replaced with an analog such as 2'-deoxy-7-deazaguanosine.

The CpG sequence may be directed to TLR9, such as the motif GTCGTT or TTCGTT. The CpG sequence may be specific for inducing a Th1 immune response, such as a CpG-A ODN, or it may be more specific for inducing a B cell response, such a CpG-B ODN. In embodiments, the CpG is a CpG-A ODN.

In embodiments, the CpG oligonucleotide may be constructed so that the 5' end is accessible for receptor recognition. Optionally, two CpG oligonucleotide sequences may be attached at their 3' ends to form "immunomers."

(4) ADP-Ribosylating Toxins and Detoxified Derivatives Thereof.

Bacterial ADP-ribosylating toxins and detoxified derivatives thereof may be used as adjuvants. In embodiments, the protein may be derived from *E. coli* (i.e., *E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. In embodiments, the adjuvant is a detoxified LT mutant such as LT-K63, LT-R72, and LTR192G.

Bioadhesives and Mucoadhesives

Bioadhesives and mucoadhesives may also be used as adjuvants. Suitable bioadhesives include esterified hyaluronic acid microspheres or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants. E.g., WO99/27960.

Muramyl Peptides

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-s-n-glycero-3-hydroxyphosphoryloxy)-ethylamine MTP-PE).

Imidazoquinoline Compounds.

Examples of imidazoquinoline compounds suitable for use as adjuvants include Imiquimod and its analogues (see, e.g., U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612).

Thiosemicarbazone Compounds.

Examples of thiosemicarbazone compounds, as well as methods of formulating, manufacturing, and screening for compounds all suitable for use as adjuvants include those described in WO04/60308. The thiosemicarbazones are particularly effective in the stimulation of human peripheral blood mononuclear cells for the production of cytokines, such as TNF-α

Tryptanthrin Compounds.

Examples of tryptanthrin compounds, as well as methods of formulating, manufacturing, and screening for compounds all suitable for use as adjuvants as disclosed herein include those described in WO04/64759. The tryptanthrin compounds are particularly effective in the stimulation of human peripheral blood mononuclear cells for the production of cytokines, such as TNF-α.

Combinations of aspects of one or more of the adjuvants identified above may be applied to the compositions as disclosed herein. For example, the following adjuvant compositions may be used:

(1) a saponin and an oil-in-water emulsion (WO99/11241); (2) a saponin (e.g., QS21)+a non-toxic LPS derivative (e.g., 3dMPL) (see WO94/00153); (3) a saponin (e.g., QS21)+a non-toxic LPS derivative (e.g., 3dMPL)+a cholesterol; (4) a saponin (e.g., QS21)+3dMPL+IL-12 (optionally+a sterol) (WO98/57659); (5) combinations of 3dMPL with, for example, QS21 and/or oil-in-water emulsions (See European patent applications 0835318, 0735898 and 0761231); (6) SAF, containing 10% Squalane, 0.4% TWEEN 80™, 5% pluronic-block polymer L121, and thr-MDP, either microfluidized into a submicron emulsion or vortexed to generate a larger particle size emulsion. (7) RIBI™ adjuvant system (RAS), (Ribi Immunochem) containing 2% Squalene, 0.2% TWEEN 80™, and one or more bacterial cell wall components from the group consisting of monophosphorylipid A (MPL), trehalose dimycolate (TDM), and cell wall skeleton (CWS), MPL+CWS (DETOX™); and (8) one or more mineral salts (such as an aluminum salt)+a non-toxic derivative of LPS (such as 3dPML). (9) one or more mineral salts (such as an aluminum salt) and one or more immunostimulatory oligonucleotides (such as a nucleotide sequence including a CpG motif) and one or more detoxified ADP-ribosylating toxins (such as LT-K63 and LT-R72), (10) inulin and inulin acetate formulations (see, e.g., WO 2013/110050, herein incorporated in its entirety).

Additional Antigens

Compositions of the as disclosed herein optionally may comprise one or more additional polypeptide antigens which are not derived from ASF viral proteins. Such antigens include bacterial, viral, or parasitic antigens.

In some embodiments, an ASF viral antigen is combined with one or more antigens including, but not limited to, antigens derived from a bacteria or virus, such as Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV), *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli.*

In other embodiments, an ASF viral antigen is combined with one or more antigens including, but not limited to, *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae, Orthomyxovirus* (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV).

In other embodiments, an ASF viral antigen is combined with one or more antigens which are useful in a vaccine designed to protect individuals against pathogens that cause diarrheal diseases. Such antigens include, but are not limited to, rotavirus, *Shigella* spp., enterotoxigenic *Escherichia coli* (ETEC), *Vibrio cholerae,* and *Campylobacter jejuni* antigens. In embodiments, one or more Norovirus antigens may be derived from Norwalk virus, Snow Mountain virus, and/or Hawaii virus are combined with a rotavirus antigen in an immunogenic composition.

Antigens which may find use with the present compositions include, but are not limited to, one or more of the following antigens set forth below, or antigens derived from one or more of the pathogens set forth below:

Bacterial Antigens

Suitable Bacterial antigens as disclosed herein include proteins, polysaccharides, lipopolysaccharides, and outer membrane vesicles which may be isolated, purified or derived from a bacteria. In addition, bacterial antigens may include bacterial lysates and inactivated bacteria formulations. Bacteria antigens may be produced by recombinant expression. Bacterial antigens include epitopes which may be exposed on the surface of the bacteria during at least one stage of its life cycle. Bacterial antigens may be conserved across multiple serotypes. Bacterial antigens include antigens derived from one or more of the bacteria set forth below as well as the specific antigens examples identified below.

*Neisseria meningitides:* Meningitides antigens may include proteins (such as those identified in References 1-7), saccharides (including a polysaccharide, oligosaccharide or lipopolysaccharide), or outer-membrane vesicles purified or derived from *N. meningitides* serogroup such as A, C, W135, Y, and/or *B. Meningitides* protein antigens may be selected from adhesions, autotransporters, toxins, Fe acquisition proteins, and membrane associated proteins (e.g., integral outer membrane protein).

*Streptococcus pneumoniae: Streptococcus pneumoniae* antigens may include a saccharide (including a polysaccharide or an oligosaccharide) and/or protein from *Streptococcus pneumoniae.* Saccharide antigens may be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens may be selected from a protein identified in WO 98/18931, WO 98/18930, U.S. Pat. Nos. 6,699,703, 6,800, 744, WO 97/43303, and WO 97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens may include a protein identified in WO 02/34771 or WO 2005/032582 (including GAS 40), fusions of fragments of GAS M proteins (including those described in WO 02/094851), fibronectin binding protein (Sfb1), Streptococcal heme-associated protein (Shp), and Streptolysin S (SagA).

*Moraxella catarrhalis: Moraxella* antigens include antigens identified in WO 02/18595 and WO 99/58562, outer membrane protein antigens (HMW-OMP), C-antigen, and/or LPS.

*Bordetella pertussis: Pertussis* antigens include petussis holotoxin (PT) and filamentous haemagglutinin (FHA) from *B. pertussis,* optionally also combination with pertactin and/or agglutinogens 2 and 3 antigen.

*Staphylococcus aureus: Staph aureus* antigens include *S. aureus* type 5 and 8 capsular polysaccharides optionally conjugated to nontoxic recombinant *Pseudomonas aeruginosa* exotoxin A, such as STAPHVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis: S. epidermidis* antigens include slime-associated antigen (SAA).

*Clostridium tetani* (Tetanus): Tetanus antigens include tetanus toxoid (TT), may be used as a carrier protein in conjunction/conjugated with the compositions of the present disclosure.

*Cornynebacterium diphtheriae* (Diphtheria): Diphtheria antigens include diphtheria toxin, including detoxified, such as $CRM_{197}$. Additionally, antigens capable of modulating, inhibiting or associated with ADP ribosylation are contemplated for combination/co-administration/conjugation with the compositions of the present disclosure. The diphtheria toxoids may be used as carrier proteins.

*Haemophilus influenzae* B (Hib): Hib antigens include a Hib saccharide antigen.

*Pseudomonas aeruginosa: Pseudomonas* antigens include endotoxin A, Wzz protein, *P. aeruginosa* LPS, more particularly LPS isolated from PAO1 (O5 serotype), and/or Outer Membrane Proteins, including Outer Membrane Proteins F (OprF).

*Legionella pneumophila.* Bacterial antigens may be derived from *Legionella pneumophila.*

*Streptococcus agalactiae* (Group B *Streptococcus*): Group B *Streptococcus* antigens include a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neiserria gonorrhoeae: Gonorrhoeae* antigens include Por (or porin) protein, such as PorB, a transferring binding protein, such as TbpA and TbpB, a opacity protein (such as Opa), a reduction-modifiable protein (Rmp), and outer membrane vesicle (OMV) preparations (see e.g., WO99/24578, WO99/36544, WO99/57280, WO02/079243).

*Chlamydia trachomatis: Chlamydia trachomatis* antigens include antigens derived from serotypes A, B, Ba and C (agents of trachoma, a cause of blindness), serotypes $L_1$, $L_2$ & $L_3$ (associated with *Lymphogranuloma venereum*), and serotypes, D-K. *Chlamydia trachomas* antigens may also include an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include TmpA antigen.

*Haemophilus ducreyi* (causing chancroid): Ducreyi antigens include outer membrane protein (DsrA).

*Enterococcus faecalis* or *Enterococcus faecium:* Antigens include a trisaccharide repeat or other *Enterococcus* derived antigens provided in U.S. Pat. No. 6,756,361.

*Helicobacter pylori: H. pylori* antigens include Cag, Vac, Nap, HopX, HopY and/or urease antigen.

*Staphylococcus saprophyticus:* Antigens include the 160 kDa hemagglutinin of *S. saprophyticus* antigen.

*Yersinia enterocolitica* Antigens include LPS.

*E. coli: E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC).

*Bacillus anthracis* (anthrax): *B. anthracis* antigens are optionally detoxified and may be selected from A-components (lethal factor (LF) and edema factor (EF)), both of which may share a common B-component known as protective antigen (PA).

*Yersinia pestis* (plague): Plague antigens include F1 capsular antigen.

*Mycobacterium tuberculosis:* Tuberculosis antigens include lipoproteins, LPS, BCG antigens, a fusion protein of antigen 85B (Ag85B) and/or ESAT-6 optionally formulated in cationic lipid vesicles, *Mycobacterium tuberculosis* (Mtb) isocitrate dehydrogenase associated antigens, and/or MPT51 antigens.

Rickettsia: Antigens include outer membrane proteins, including the outer membrane protein A and/or B (OmpB).

*Listeria monocytogenes.* Bacterial antigens may be derived from *Listeria monocytogenes.*

*Chlamydia pneumoniae:* Antigens include those identified in WO 02/02606.

*Vibrio cholerae:* Antigens include proteinase antigens, LPS, particularly lipopolysaccharides of *Vibrio cholerae* II, O1 Inaba O-specific polysaccharides, *V. cholera* O139, antigens of IEM108 vaccine, and/or *Zonula occludens* toxin (Zot).

*Salmonella typhi* (typhoid fever): Antigens include capsular polysaccharides, including conjugates (Vi, i.e., vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins., such as antigens associated with P39 and P13 VlsE Antigenic Variation Protein.

*Porphyromonas gingivalis:* Antigens include *P. gingivalis* outer membrane protein (OMP).

*Klebsiella:* Antigens include an OMP, including OMP A, or a polysaccharide optionally conjugated to tetanus toxoid.

Further bacterial antigens of the instant disclosure may be capsular antigens, polysaccharide antigens or protein antigens of any of the above. Further bacterial antigens may also include an outer membrane vesicle (OMV) preparation. Additionally, antigens include live, attenuated, and/or purified versions of any of the aforementioned bacteria. The antigens of the present disclosure may be derived from gram-negative or gram-positive bacteria. The antigens of the present disclosure may be derived from aerobic or anaerobic bacteria.

Additionally, any of the above bacterial-derived saccharides (polysaccharides, LPS, LOS or oligosaccharides) may be conjugated to another agent or antigen, such as a carrier protein (for example CRMi97). Such conjugation may be direct conjugation effected by reductive amination of carbonyl moieties on the saccharide to amino groups on the protein, as provided in U.S. Pat. No. 5,360,897. Alternatively, the saccharides may be conjugated through a linker, such as, with succinamide or other linkages.

Viral Antigens

Viral antigens suitable for use in the compositions as disclosed include purified subunit formulations, viral proteins which may be isolated, purified or derived from a virus, and Virus Like Particles (VLPs). Viral antigens may be derived from viruses propagated on cell culture or other substrate. Alternatively, viral antigens may be expressed recombinantly. Viral antigens include epitopes which are exposed on the surface of the virus during at least one stage of its life cycle. Viral antigens may be conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). In embodiments, antigens include HA and NA.

Influenza antigens may be derived from interpandemic (annual) flu strains. Alternatively, influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. In embodiments, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Pneumovirus antigens may include F, G and M. Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (NV), Mumps, Sendai viruses, Simian virus 5, Bovine parainfluenza virus and Newcastle disease virus. In embodiments, the Paramyxovirus is PIV or Mumps. Paramyxovirus antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Paramyxovirus proteins may include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are may be used.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In embodiments, the Enterovirus may be poliovirus. Enterovirus antigens may include one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from an Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, may be used. Togavirus antigens may be selected from E1, E2, E3, C, NSP-1, NSPO-2, NSP-3 or NSP-4. Togavirus antigens include E1, E2 or E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, *Powassan encephalitis*. Flavivirus antigens may be selected from PrM, M, C, E, NS-1, NS-2a, NS2b, NS3, NS4a, NS4b, and NS5. Flavivirus antigens may include PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the non-structural regions.

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L), non-structural proteins (NS). Commercially available Rabies virus vaccine comprise killed virus grown on human diploid cells or fetal rhesus lung cells.

Caliciviridae; Viral antigens may be derived from Calciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). In embodiments, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (e.g., p55 gag and gp140v delete). HIV antigens may be derived from one or more of the following strains: $HIV_{IIIb}$, $HIV_{SF2}$, $HIV_{LAV}$, $HIV_{LAI}$, $HIV_{MN}$, HIV-$1_{CM235}$, HIV-$1_{US4}$.

Reovirus: Viral antigens may be derived from a Reovirus, such as an Orthoreovirus, a Rotavirus, an Orbivirus, or a Coltivirus. Reovirus antigens may be selected from structural proteins λ1, λ2, λ3, μ1, μ2, σ1, σ2, or σ3, or nonstructural proteins σNS, μNS, or σ1s. Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Rotavirus antigens may include VP4 (or the cleaved product VP5 and VP8), and VP7. See, e.g., WO 2005/021033, WO 2003/072716, WO 2002/11540, WO 2001/12797, WO 01/08495, WO 00/26380, WO 02/036172; herein incorporated by reference in their entireties.

Parvovirus: Viral antigens may be derived from a Parvovirus, such as Parvovirus B19. Parvovirus antigens may be selected from VP-1, VP-2, VP-3, NS-1 and NS-2. In embodiments, the Parvovirus antigen is capsid protein VP-2.

Delta hepatitis virus (HDV): Viral antigens may be derived HDV, particularly .delta.-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. In embodiments, HPV antigens are derived from serotypes 6, 11, 16 or 18. HPV antigens may include capsid proteins (L1) and (L2), or E1-E7, or fusions thereof. Polyomyavirus viruses include BK virus and JK virus. Polyomavirus antigens may be selected from VP1, VP2 or VP3.

Circovirus: Antigens may be derived from Circoviruses, such as Porcine circovirus (PCV) 1, PCV 2, PCV 3, and PCV 4.

Fungal Antigens

Suitable fungal antigens may be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. album, var. discoides, var. ochraceum, *Trichophyton violaceum,* and/or *Trichophyton faviforme.*

Fungal pathogens may be derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp., *Mucor* spp., *Absidia* spp., *Mortierella* spp., *Cunninghamella* spp., *Saksenaea* spp., *Alternaria* spp., *Curvularia* spp., *Helminthosporium* spp., *Fusarium* spp., *Aspergillus* spp., *Penicillium* spp., *Monolinia* spp., *Rhizoctonia* spp., *Paecilomyces* spp., *Pithomyces* spp., and *Cladosporium* spp.

Processes for producing a fungal antigens are well known in the art (see U.S. Pat. No. 6,333,164). In one method, a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Respiratory Antigens

The compositions of the as disclosed herein may include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacteria which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis,* and *Moraxella catarrhalis.* Examples of specific antigens derived from these pathogens are described above.

The immunogenic compositions as disclosed herein may be prepared in various forms. For example, the compositions may be prepared as injectables, either as liquid solutions or suspensions. Solid forms suitable for solution in, or suspension in, liquid vehicles prior to injection may also be prepared (e.g., a lyophilized composition or a spray-freeze dried composition). The composition may be prepared for topical administration e.g., as an ointment, cream or powder. The composition may be prepared for oral administration e.g., as a tablet or capsule or as a spray. The composition may be prepared for pulmonary administration e.g., as an inhaler, using a fine powder or a spray. The composition may be prepared as a suppository or pessary. The composition may be prepared for nasal, aural or ocular administration e.g., as drops. Preparation of such pharmaceutical compositions is within the general skill of the art. See, e.g., Remington's Pharmaceutical Sciences, Mack Publishing Company, Easton, Pa., 18th edition, 1990.

The composition may be in kit form, designed such that a combined composition is reconstituted just prior to administration to a patient. Such kits may comprise one or more ______ antigens or nucleic acids encoding such antigens in liquid form, and any of the additional antigens and adjuvants as described herein.

Immunogenic compositions comprising polypeptide antigens as disclosed are vaccine compositions. The pH of such compositions is between 6 and 8, about 7. The pH may be maintained by the use of a buffer. The composition may be sterile and/or pyrogen-free. The composition may be isotonic with respect to the subject. Vaccines according to the instant disclosure may be used either prophylactically or therapeutically, but will typically be prophylactic and may be used to treat animals (including farm, game, companion and laboratory mammals).

Immunogenic compositions used as vaccines comprise an immunologically effective amount of antigen(s) and/or nucleic acids encoding antigen(s), as well as any other components, as needed. By "immunologically effective amount," it is meant that the administration of that amount to an individual, either in a single dose or as part of a series, is effective for treatment or prevention. This amount varies depending upon the health and physical condition of the individual to be treated, age, the taxonomic group of individual to be treated (e.g., swine, cattle, and the like), the capacity of the individual's immune system to synthesize antibodies, the degree of protection desired, the formulation of the vaccine, the treating veterinarian's assessment of the medical situation, and other relevant factors. It is expected that the amount will fall in a relatively broad range that may be determined through routine trials.

Administration

Compositions of as disclosed herein will generally be administered directly to a subject. Direct delivery may be accomplished by parenteral injection (e.g., subcutaneously, intraperitoneally, intravenously, intramuscularly, or to the interstitial space of a tissue), or mucosally, such as by rectal, oral (e.g., tablet, spray), vaginal, topical, transdermal (see, e.g., WO99/27961) or transcutaneous (see e.g., WO02/074244 and WO02/064162), intranasal (see, e.g., WO03/028760), ocular, aural, pulmonary or other mucosal administration. Immunogenic compositions may also be administered topically by direct transfer to the surface of the skin. Topical administration may be accomplished without utilizing any devices, or by contacting naked skin with the immunogenic composition utilizing a bandage or a bandage-like device (see, e.g., U.S. Pat. No. 6,348,450).

In embodiments, the mode of administration may be parenteral, mucosal or a combination of mucosal and parenteral immunizations. In one aspect, the mode of administration is parenteral, mucosal or a combination of mucosal and parenteral immunizations in a total of 1-2 vaccinations 1-3 weeks apart. In one aspect, the route of administration includes but is not limited to oral delivery, intra-muscular delivery and a combination of oral and intra-muscular delivery.

It has already been demonstrated that mucosal and systemic immune responses to antigens, such as Helicobacter pylori antigens may be enhanced through mucosal priming followed by systemic boosting immunizations. In embodiments, the method for treating an infection by an ASF virus, comprises mucosally administering to a subject in need thereof a first immunogenic composition comprising one or more ASF viral antigens followed by parenterally administering a therapeutically effective amount of a second immunogenic composition comprising one or more ASF viral antigens.

The immunogenic composition may be used to elicit systemic and/or mucosal immunity, to elicit an enhanced systemic and/or mucosal immunity.

In embodiments, the immune response is characterized by the induction of a serum IgG and/or intestinal IgA immune response.

As noted above, prime-boost methods may be employed where one or more gene delivery vectors and/or polypeptide antigens are delivered in a "priming" step and, subsequently, one or more second gene delivery vectors and/or polypeptide antigens are delivered in a "boosting" step. In certain embodiments, priming and boosting with one or more gene delivery vectors or polypeptide antigens described herein is followed by additional boosting with one or more polypeptide-containing compositions (e.g., polypeptides comprising ASF viral antigens).

In any method involving co-administration, the various compositions may be delivered in any order. Thus, in embodiments including delivery of multiple different compositions or molecules, the nucleic acids need not be all delivered before the polypeptides. For example, the priming step may include delivery of one or more polypeptides and the boosting comprises delivery of one or more nucleic acids and/or one or more polypeptides. Multiple polypeptide administrations may be followed by multiple nucleic acid administrations or polypeptide and nucleic acid administrations may be performed in any order. Thus, one or more of the gene delivery vectors described herein and one or more of the polypeptides described herein may be co-administered in any order and via any administration route. Therefore, any combination of polynucleotides and polypeptides described herein may be used to elicit an immune reaction.

Dosage Regime

Dosage treatment may be according to a single dose schedule or a multiple dose schedule. Multiple doses may be used in a primary immunization schedule and/or in a booster immunization schedule. In a multiple dose schedule, the various doses may be given by the same or different routes, e.g., a parenteral prime and mucosal boost, a mucosal prime and parenteral boost, and the like.

In embodiments, the dosage regime enhances the avidity of the antibody response leading to antibodies with a neutralizing characteristic. An in-vitro neutralization assay may be used to test for neutralizing antibodies.

There is a strong case for a correlation between serum antibody levels and protection from disease caused by ASF virus.

Tests to Determine the Efficacy of an Immune Response

One way of assessing efficacy of therapeutic treatment involves monitoring infection after administration of a composition of the as disclosed. One way of assessing efficacy of prophylactic treatment involves monitoring immune responses against the antigens in the compositions of the as disclosed after administration of the composition.

Another way of assessing the immunogenicity of the component proteins of the immunogenic compositions of the present disclosure is to express the proteins recombinantly and to screen patient sera or mucosal secretions by immunoblot. A positive reaction between the protein and the patient serum indicates that the patient has previously mounted an immune response to the protein in question—that is, the protein is an immunogen. This method may also be used to identify immunodominant proteins and/or epitopes.

Another way of checking efficacy of therapeutic treatment involves monitoring infection after administration of the compositions of the present disclosure. One way of checking efficacy of prophylactic treatment involves monitoring immune responses both systemically (such as monitoring the level of IgG1 and IgG2a production) and mucosally (such as monitoring the level of IgA production) against the antigens in the compositions of the present disclosure after administration of the composition. Typically, serum specific antibody responses are determined post-immunization but pre-challenge whereas mucosal specific antibody body responses are determined post-immunization and post-challenge.

The immunogenic compositions of the present disclosure may be evaluated in in vitro and in vivo animal models prior to host. Particularly useful mouse models include those in which intraperitoneal immunization is followed by either intraperitoneal challenge or intranasal challenge.

The efficacy of immunogenic compositions of the present disclosure may also be determined in vivo by challenging animal models of infection, e.g., guinea pigs or mice or rhesus macaques, with the immunogenic compositions. The immunogenic compositions may or may not be derived from the same strains as the challenge strains. In embodiments, the immunogenic compositions may be derivable from the same strains as the challenge strains.

In vivo efficacy models include but are not limited to: (i) A murine infection model using human strains; (ii) a murine disease model which is a murine model using a mouse-adapted strain, such as strains which are particularly virulent in mice and (iii) a primate model using human isolates. A human challenge model, which is supported by the NIH and Center for Disease Control (CDC) is also available.

The immune response may be one or both of a TH1 immune response and a TH2 response. The immune response may be an improved or an enhanced or an altered immune response. The immune response may be one or both of a systemic and a mucosal immune response. In embodiments, the immune response is an enhanced systemic and/or mucosal response.

An enhanced systemic and/or mucosal immunity is reflected in an enhanced TH1 and/or TH2 immune response. In embodiments, the enhanced immune response includes an increase in the production of IgG1 and/or IgG2a and/or IgA. In embodiments, the mucosal immune response is a TH2 immune response. In one aspect, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. In embodiments, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. In embodiments, the enhanced TH1 immune response will include an increase in IgG2a production.

Immunogenic compositions of the present disclosure, in particular, immunogenic composition comprising one or more antigens of the present disclosure may be used either alone or in combination with other antigens optionally with an immunoregulatory agent capable of eliciting a Th1 and/or Th2 response.

The immunogenic composition of the present disclosure may also comprise one or more immunoregulatory agents, such as a mineral salt, such as an aluminum salt and an oligonucleotide containing a CpG motif. In embodiments, the immunogenic composition includes both an aluminum salt and an oligonucleotide containing a CpG motif. Alternatively, the immunogenic composition includes an ADP ribosylating toxin, such as a detoxified ADP ribosylating toxin and an oligonucleotide containing a CpG motif. In one aspect, the one or more immunoregulatory agents include an adjuvant. The adjuvant may be selected from one or more of the group consisting of a TH1 adjuvant and TH2 adjuvant, further discussed above.

The immunogenic compositions of the present composition may elicit both a cell mediated immune response as well as a humoral immune response in order to effectively address an infection. This immune response may induce long lasting (e.g., neutralizing) antibodies and a cell mediated immunity that may quickly respond upon exposure to one or more infectious antigens. By way of example, evidence of neutralizing antibodies in a subject's blood samples is considered as a surrogate parameter for protection since their formation is of decisive importance for virus elimination in TBE infections.

Use of the Immunogenic Compositions as Medicaments

The instant disclosure also provides a composition for use as a medicament. The medicament may be able to raise an immune response in a mammal (i.e., it is an immunogenic composition) and may be a vaccine. The present disclosure also provides the use of the instant compositions in the manufacture of a medicament for raising an immune response in a mammal. The medicament may be a vaccine. In embodiments, the vaccine is used to prevent and/or treat an intestinal infection such as gastroenteritis, including acute gastroenteritis. The gastroenteritis may result from an imbalance in ion and/or water transfer resulting in both watery diarrhea and/or intestinal peristalisis and/or motility (vomiting).

The instant disclosure provides methods for inducing or increasing an immune response using the compositions described above. The immune response may be protective and may induce antibodies and/or cell-mediated immunity (including systemic and mucosal immunity). Immune responses include booster responses.

The present disclosure also provides a method for raising an immune response in a mammal comprising the step of administering an effective amount of a composition of the instant disclosure. The immune response may be protective and may involve antibodies and/or cell-mediated immunity. In embodiments, the immune response includes one or both of a TH1 immune response and a TH2 immune response. The method may raise a booster response.

Kits

The present disclosure also provides kits comprising one or more containers of compositions as described herein. Compositions may be in liquid form or may be lyophilized, as may individual antigens. Suitable containers for the compositions include, for example, bottles, vials, syringes, and test tubes. Containers may be formed from a variety of materials, including glass or plastic. A container may have a sterile access port (for example, the container may be an intravenous solution bag or a vial having a stopper pierceable by a hypodermic injection needle).

The kit may further comprise a second container comprising a pharmaceutically-acceptable buffer, such as phosphate-buffered saline, Ringer's solution, or dextrose solution. It may also contain other materials useful to the end-user, including other pharmaceutically acceptable formulating solutions such as buffers, diluents, filters, needles, and syringes or other delivery device. The kit may further include a third component comprising an adjuvant.

The kit may also comprise a package insert containing written instructions for methods of inducing immunity or for treating infections. The package insert may be an unapproved draft package insert or may be a package insert approved by the Food and Drug Administration (FDA) or other regulatory body.

In embodiments, a delivery device is pre-filled with the immunogenic compositions as disclosed herein.

Methods of Producing ASF virus-Specific Antibodies

The ASF viral polypeptides described herein may be used to produce ASF virus-specific polyclonal and monoclonal antibodies that specifically bind to/are selective for ASF viral antigens, respectively. Polyclonal antibodies may be produced by administering an ASF viral polypeptide to a mammal, such as a mouse, a rabbit, a goat, or a horse. Serum from the immunized animal is collected and the antibodies are purified from the plasma by, for example, precipitation with ammonium sulfate, followed by chromatography, including affinity chromatography. Techniques for producing and processing polyclonal antisera are known in the art.

Monoclonal antibodies directed against ASF viral-specific epitopes present in the polypeptides may also be readily produced. Normal B cells from a mammal, such as a mouse, immunized with an ASF viral polypeptide, may be fused with, for example, HAT-sensitive mouse myeloma cells to produce hybridomas. Hybridomas producing ASF viral-specific antibodies may be identified using RIA or ELISA and isolated by cloning in semi-solid agar or by limiting dilution. Clones producing ASF viral-specific antibodies are isolated by another round of screening.

Antibodies, i.e., monoclonal and antibodies from polyclonal sera (polyclonal), which are directed against ASF viral epitopes, are particularly useful for detecting the presence of ASF viral antigens in a sample, such as a serum sample from a ASF virus-infected subject. An immunoassay for an ASF viral antigen may utilize one antibody or several antibodies. An immunoassay for an ASF viral antigen may use, for example, a monoclonal antibody directed towards an ASF viral epitope, a combination of monoclonal antibodies directed towards epitopes of one ASF viral polypeptide, monoclonal antibodies directed towards epitopes of different ASF viral polypeptides, polyclonal antibodies directed towards the same ASF viral antigen, polyclonal antibodies directed towards different ASF viral antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate ASF viral particles or antigens by immunoaffinity columns. The antibodies may be affixed to a solid support by, for example, adsorption or by covalent linkage so that the antibodies retain their immunoselective activity. Optionally, spacer groups may be included so that the antigen binding site of the antibody remains accessible. The immobilized antibodies may then be used to bind ASF viral particles or antigens from a biological sample, such as blood or plasma. The bound ASF viral particles or antigens are recovered from the column matrix by, for example, a change in pH.

All patent literature cited in the instant disclosure is incorporated by reference in their entireties herein.

EXAMPLES

Example 1. Baculovirus Protein Subunit Production

The Recombinant Baculovirus protein expression system was based on a nucleic acid sequence for targeted ASF viral proteins. The final sequence was optimized for expression in in-house Spodoptera frugiperda insect cells (Sf9) to ensure that appropriate restriction endonuclease sites are present at the termination of the sequence.

A pBacPAK8 cloning vector (Clontech Laboratories, Inc., Mountain View, CA) was used to prepare a plasmid vector containing the target sequence. The plasmid vector contains flanking sequences homologous to the linear BestBac 2.0 Baculovirus vector (Expression Systems, Davis, CA), such that when the plasmid containing the ASF viral p30, p30/p54, p72 and/or hemagglutinin insert was co-transfected into Sf9 cells with the linear BestBac 2.0 virus Baculovirus backbone (Expression Systems, Davis, CA), homologous recombination exchanges the H3 insert for the polyhedrin gene of the Baculovirus. The resulting Baculovirus containing the ASF viral sequence expressed under control of the polyhedrin promoter was then harvested. Cells and virus were grown in culture media obtained from Expression Systems (Media ES 99-300) formulated without animal origin ingredients. Gentamicin solution is added to a final concentration of 10 μg/ml from purchased stock solution (Gibco Cat #15710). At final harvest, infected cultures were centrifuged to remove the cells and the supernatant collected. The supernatant was processed through 0.2-micron sterile disposable filter. The premaster culture was titered to determine final concentration.

Sf9 cells are scaled up to production quantities utilizing glass or sterile disposable plastic vessel volumes. Upon reaching the final cell culture volume required for production, virus infection occurs in the same vessel as the final passage of cells was prepared. Culture mixing is achieved through shaking/rocking of the container or utilizing low shear type impeller design. Mixing speed and intensity is adjusted to maintain cells in suspension without creating excess shear or foaming which will cause cell disruption.

Viral fluids are inactivated with Beta-propiolactone (BPL) at a final concentration of 0.2-0.3%. Prior to inactivation, the pH of the disrupted fluids are adjusted to 7.5-8.0 using 2-10N NaOH as base or 10-38% HCl or 10% Nitric acid as acid. The disrupted fluids are allowed to warm to room temperature for 1-18 hours prior to the addition of BPL. BPL is added at the concentration specified above, with mixing. After the addition of BPL, the viral fluids are transferred to an inactivation container utilizing a “bottom to bottom” transfer process to ensure that all fluids have come into contact with BPL. The disrupted fluids are incubated at 17-27° C. for 18-48 hours with agitation. After the inactivation process is complete, the pH is adjusted to 7.0-7.5 with acid or base as mentioned above. The inactivated virus fluids are stored at 2-8° C. until further processing. The antigen is prepared with Water/Oil/Water (WOW) adjuvant.

Example 2. Field Evaluation of ASF Antigen Based Vaccine

The antigens were manufactured as described above (i.e., Hemagglutinin, SEQ ID NO:17 and p30/p54 fusion protein, SEQ ID NO:6).

Eight (8) commercial farms in were selected for enrollment to this study. The animals used in the farm came from other farms not infected with ASF.

Experimental Design

Inclusion, Exclusion and Withdrawal Criteria

All animals used in this trial were apparently healthy at the start of the trial. Any pig that was suffering illness, ill thrift or significant trauma, or lameness were to be excluded as per normal management practice.

Randomization

Pigs that met all the inclusion and had none of the exclusion criteria were randomly allocated into one of the 2 treatment groups or the placebo group. Equal number of pigs from each of the treatment groups and a twenty five (25) percentage of placebo were assigned to each pen.

Handling of Sick

Sick animals were treated as per the farm standard operating procedures or treatment protocols. Morbidities of any cause were noted and recorded.

Blood from animals suspected of ASF (severe lethargy, discoloration of the extremities, etc.) and or dead animals were collected for initial screening for the presence of ASF antigens using rapid test kits and the same blood sample was subsequently submitted for confirmatory testing.

Treatment Groups:

| Treatment | Vaccine | Composition | Number of Pigs | Vaccinations (Day) | Blood (Serum) Sample Collection |
|---|---|---|---|---|---|
| 1 | ASF antigen-based vaccine 1 | p30/p54 fusion | ~100 | 0, 21 | 0, 21, 42, 84 |
| 2 | ASF antigen-based vaccine 2 | P30/p54 fusion + Hemagglutinin | ~100 | 0, 21 | 0, 21, 42, 84 |
| Control | None | N/A | ~50 | 0, 21 | 0, 21, 42, 84 |

The individual animal was the experimental unit. Each pig was double-tagged (one tag in each ear) and co-mingled with an equal number of pigs from different vaccinated groups and control in each pen. The pens used were in one single building.

Vaccination

Animals in the vaccinated groups received one of the two vaccines and given two doses of 1 mL with an interval of 3 weeks between doses.

Blood Collection for Serological Testing:

| | Experimental Group | Number of Pigs | Samples per Sample Collection Time | Blood (Serum) Sample Collection | Total Blood Samples per farm |
|---|---|---|---|---|---|
| Protocol 1 | Treatment 1 | ~100 | 5 | 0, 21, 42, 84 | 20 |
| | Treatment 2 | ~100 | 5 | 0, 21, 42, 84 | 20 |
| | Control | ~50 | 3 | 0, 21, 42, 84 | 12 |
| | | Samples per farm | | | 52 |

Data for Collection and Results

Animals were monitored daily for adverse events starting on day 0 and continuing until 21 days post second vaccination. All adverse events were recorded. Special attention was made to: swelling/inflammation, soreness, redness, abscesses, lumps, lesions, and warmth at the injection site. Other observations to record included, but were not limited to: lameness, lack of thriftiness, anorexia, and general lack of normal behavior.

All serum samples were tested for the presence of antibodies to ASF p54 antigen using Biochek African Swine Fever Antibody Test Kit. This test was to determine seroconversion to the experimental vaccines by testing immune response to the p54 portion of the p30/p54 fusion protein in the vaccine formulation.

All samples were tested for the presence of antibodies to ASF p72 antigen using Ingenza PPA CROM. This served as the screening test to detect if the animals in the experiment had been exposed to ASF virus.

All samples were tested for the presence of antibodies to ASF p30(32), p62, and p72 antigen using the ID Screen ASF Indirect ELISA. This test was to determine seroconversion to the experimental vaccines by testing the immune response to the p30 portion of the p30/p54 fusion protein in the vaccine formulation.

Of the 3 assays run on the samples collected during the duration of the study, 2 of them were for assessing the immunological response of the animal to vaccination, Bio-check and ID Screen. Each of these tests measured a different fraction of the p30/p54 fusion protein in the vaccine formulation. The ID Screen assay measuring the p30(32) antigen, appeared demonstrate an immune response during the course of the vaccination and observation period of the study.

Conclusions

Immune Response

When assessing the immunological response of the animals that were administered the test vaccine containing the p30/p54 fusion protein in both treatment groups 1 and 2. It can be concluded that vaccination did illicit an immune response to the p30(32) antigen tested for in the ID Screen Indirect kit. An increase in antibody presence was detected in naive farms beginning around study day 21 for treatment group 1 with antibody concentrations being very similar between both treatment groups at the blood collection on study day 42.

Based on these results, the formulation does illicit an immune response directed to ASF antigen.

Although the invention has been described with reference to the above examples, it will be understood that modifications and variations are encompassed within the spirit and scope of the invention. Accordingly, the invention is limited only by the following claims.

We claim herein:

1. A method for producing African Swine Fever (ASF) virus-derived immunogenic polypeptides and/or peptides comprising:

culturing a host cell transformed with a nucleic acid under conditions which induce expression of the polypeptides and/or peptides, wherein said polypeptides and/or peptides comprise the amino acid sequence as set forth in SEQ ID NOs:6, 8, 10, 12, 17 or combinations thereof; and optionally, mixing or co-expressing said immunogenic polypeptides and/or peptides with one or more adjuvants.

2. The method of claim 1, wherein at least one of the one or more adjuvants is a water/oil/water adjuvant.

3. The method of claim 2, wherein the immunogenic polypeptides and/or peptides are formulated into a recombinant vaccine, and wherein such expressed polypeptides and/or peptides are generated using baculovirus/insect cell methodology.

4. The method of claim 1, wherein the polypeptides and/or peptides comprise the amino acid sequence as set forth in SEQ ID NOs:6 and 8.

5. The method of claim 2, wherein the nucleic acid encoding the ASF virus derived immunogenic polypeptides and/or peptides is prepared by chemical synthesis.

6. The method of claim 5, wherein the nucleic acid encoding the ASF derived immunogenic polypeptides and/or peptides is generated using a primer-based amplification method.

7. The method of claim 6, wherein the primer-based amplification method is PCR.

8. An immunogenic composition comprising the polypeptide as set forth in SEQ ID NOs: 6, 8, 10, 12, 17 or combinations thereof

9. A method of eliciting an immunological response in a subject comprising administering a composition as set forth in claim 8.

10. The method of claim 9, further comprising administering an adjuvant.

11. The method of claim 10, wherein administering said immunogenic composition to said subject is via topical, parenteral or mucosal administration.

12. The method of claim 9, wherein said administration is by multiple administrations.

13. The method of claim 12, wherein a first immunogenic composition and a second immunogenic composition are the same.

14. The method of claim 12, wherein a first immunogenic composition and the second immunogenic composition are different.

15. A method of immunizing against infection by an African Swine Fever virus comprising administering to a subject in need thereof a therapeutically effective amount of an immunogenic composition of claim 8.

16. The method of claim 15, wherein he composition comprises an ASF virus p30/p54 fusion protein.

17. The method of claim 15, wherein the composition comprises an ASF virus hemagglutinin protein.

18. The method of claim 15, wherein the composition comprises administering a composition comprising ASF virus p30/p54 fusion protein and ASF virus hemagglutinin protein.

19. The method of claim 15, wherein the subject is a pig.

20. The method of claim 18, wherein the proteins are administered substantially simultaneously or sequentially.

* * * * *